United States Patent [19]

Belohlavek

[11] Patent Number: 5,871,019
[45] Date of Patent: Feb. 16, 1999

[54] FAST CARDIAC BOUNDARY IMAGING

[75] Inventor: Marek Belohlavek, Rochester, Minn.

[73] Assignee: Mayo Foundation for Medical Education and Research, Rochester, Minn.

[21] Appl. No.: 935,128

[22] Filed: Sep. 22, 1997

Related U.S. Application Data

[60] Provisional application No. 60/026,541 Sep. 23, 1996.

[51] Int. Cl.[6] ........................................................ A61B 8/00
[52] U.S. Cl. ............................ 128/916; 600/450; 600/441
[58] Field of Search ..................................... 600/443, 442, 600/441; 128/916, 660.04, 660.07

[56] References Cited

U.S. PATENT DOCUMENTS

| 5,159,931 | 11/1992 | Pini ........................................... 600/441 |
| 5,239,591 | 8/1993 | Ranganath .................................. 382/6 |
| 5,435,310 | 7/1995 | Sheehan et al. ....................... 128/653.1 |
| 5,485,845 | 1/1996 | Verdonk et al. .................... 128/662.06 |
| 5,487,388 | 1/1996 | Rello et al. ......................... 128/660.09 |
| 5,568,811 | 10/1996 | Olstad ................................. 128/660.07 |
| 5,577,506 | 11/1996 | Dias .................................... 128/662.03 |

OTHER PUBLICATIONS

Martin et al., Methodology For Three–Dimensional Reconstruction Of The Left Ventricle From Transesophageal Echocardiograms, Ultrasound in Medical and biology, vol. 19. No. 1. pp. 27–38, 1993.
McCann et al., A method for three–dimensional ultrasonic imaging of the heart in vivo, Dynamic Cardiovascular Imaging, vol. 1, No. 2, pp. 97–109, 1987.
Learning–Based Ventricle Detection from Cardiac MR and CT Images, IEEE Transactions on Medical Imaging, vol. 16, No. 4, Aug. 1997, Weng, et al.
The Self–Organizing Map, Proceedings of the IEEE, Vo. 78, No. 9, Sep. 1990, Teuvo Kohonen.
Detecting Left Ventricular Endocardial and Epicardial Boundaries by Digital Two–Dimensional Echocardiography, IEEE Transactions on Medical Imaging, vol. 7, No. 2, Jun. 1988, Chu, et al.
Classifying Tissue and Structure in Echocardiograms, IEEE Engineering in Medicine and Biology, pp. 754–760, Nov./Dec. 1994, Brotherton, et al.
Recovery of the 3–D Shape of the Left Ventricle from Echocardiographic Images, IEEE Transcations on Medical Imaging, vol. 14, No. 2, Jun. 1995, pp. 301–317, Coppini, et al.
Automatic Initial Estimatin of the Left Ventricular Myocardial Midwall in Emission Tomograms Using Kohonen Maps, IEEE Transactions on Pattern Analysis and Machine Intelligence, vol. 16, No. 3, Mar. 1994, Manhaeghe, et al.
Edge Detectors Based on Nonlinear Filters, IEEE Transactions on Pattern Analysis and Machine Intelligence, vol. PAMI–8, No. 4, Jul. 1986, Pitas, et al.

Primary Examiner—Marvin M. Lateef
Assistant Examiner—Ali M. Imam
Attorney, Agent, or Firm—Quarles & Brady, LLP

[57] ABSTRACT

An ultrasonic transducer acquires a series of ultrasound tomograms as it continuously rotates through a range of angles. When positioned in a left ventricular long axis view, serial sectional slices are acquired within 6 seconds from which a 3D image is reconstructed. The boundary of the left ventricle is identified in this 3D image using a reference database produced by a learning process that captures expert knowledge of left ventricle cavity shapes.

2 Claims, 5 Drawing Sheets

FAST CARDIAC BOUNDARY IMAGING

STATEMENT REGARDING FEDERALLY SPONSORED RESEARCH

This invention was made with U.S. Government support awarded by the National Institute of Health (NIH) Grant No.: HL 52494. The U.S. Government has certain rights in this invention.

CROSS REFERENCE TO RELATED APPLICATION

This application is based on provisional application Ser. No. 60/026,541, filed on Sep. 23, 1996 and entitled "FAST CARDIAC BOUNDARY IMAGING".

BACKGROUND OF THE INVENTION

The field of the invention is echocardiography and particularly, the measurement of left ventricular volume using 3D ultrasound data.

Assessment of left ventricular ("LV") function is clinically important. Diastolic and systolic volumes and derived parameters, such as ejection fraction, are generally accepted indicators of LV function. Echocardiography is a widely available clinical method which allows measurement of these parameters. Precision and accuracy of echocardiographic measurements is typically compromised by user's subjectivity, limited windows of access for obtaining echocardiographic scans, and ultrasound signal attenuation and scattering resulting in image artifacts.

In the past decade, compared to single or biplane tomographic techniques that require geometrical assumptions about LV shape, three-dimensional (3D) echocardiography has been shown to provide more precise and accurate evaluation of cardiac volumes. This is particularly relevant in patients with irregular LV geometry, detected during an initial echocardiographic study through multiple tomographic projections. So far, however, the 3D technique has been limited to experimental use due to cumbersome image acquisition (i.e. restricted access windows, long acquisition times, custom probes and special probe holders), time consuming and subjective data processing (i.e. digitization from video tapes and manual delineation of boundaries in numerous serial tomograms), the use of special projections (i.e. parallel or rotational scans with specific incremental steps), and mapping of endo- and epicardium to multiparameter (i.e. computationally intense and subjective for required adjustment of multiple features) models and allowed only limited objective utilization of a priori knowledge about LV geometry.

The concept of 3D ultrasound data acquisition was first described by Baum and Greenwood in 1961, (G. Baum and J. Greenwood, "Orbital Lesion Location by Three-Dimensional Ultrasonography", N.Y. State J Med, 61:4149, 4157, 1961). They obtained serial parallel ultrasound images of the human orbit and created a 3D display by stacking together sequential photographic plates bearing the ultrasound images.

Using a transthoracic echocardiographic (TTE) approach, Dekker et al., (D. L. Dekker, R. L. Piziali and D. Dong Jr., "A System For Ultrasonically Imaging The Human Heart In Three Dimensions", Comput. Biomed. Res., 7:544–553, 1974), were among the first to obtain a 3D computer matrix of ECG and respiratory gated image data with a probe attached to a mechanical arm which tracked its spatial motion. Images were subsequently displayed as selected 2D sections. Geiser et al., (E. A. Geiser, L. G. Christie, Jr., D. A. Conetta, C. R. Conit and G. S. Gossman, "A Mechanical Arm For Spatial Registration Of Two-Dimensional Echocardiographic Sections", Cathet. Cardiovasc. Diagn., 8:89–101, 1982), and other investigators have also employed mechanical location systems because of their relative simplicity and low cost.

Ghosh et al., (A. Ghosh, N. C. Nanda and G. Maurer, "Three-Dimensional Reconstruction Of Echocardiographic Images Using The Rotation Method", Ultrasound Med. Biol., 8:655–661, 1982), used a mechanical arm which permits rotation of the transducer only about its imaging axis. Rotation was registered by a precision potentiometer. Although still relying on mechanical parts, this approach introduced a fixed polar coordinate system resulting in a proportionally sampled LV contour in 30° angular increments. Several other investigators have pivoted or rotated the transthoracic transducer at a single location in an effort to obtain tomograms for 3D reconstruction of the LV from a single acceptable acoustic window. The quality of these reconstructions was often limited by the available window and variations in contact of the transducer face with the skin surface during the lengthy acquisition.

Mortiz et al., (W. E. Moritz, and P. L. Shreve, "A Microprocessor-Based Spatial-Locating System For Use With Diagnostic Ultrasound", Pro. IEEE, 64:966–974, 1976), introduced an acoustic position location system ("spark gap"). They employed this device to obtain an arbitrary series of sector scans through the heart which were used to create a computer 3D wire frame model of the LV and calculate its volume (W. E. Moritz, A. S. Pearlman, D. H. McCabe, D. K. Medema, M. E. Ainsworth and M. S. Boles, "An Ultrasonic Technique For Imaging The ventricle In Three-Dimensions And Calculating Its Volume", IEEE Trans. Biomed. Eng., 30:482–492, 1983). King and his coworkers applied this system to guided image acquisition for clinical quantitative evaluation of the LV (D. L. King, M. R. Harrison, D. L. King Jr., A. S. Gopal, R. P. Martin and A. N. DeMaria, "Improved Reproducibility Of Left Arterial And Left Ventricular Measurement By Guided Three-Dimensional Echocardiography", J. Am. Coll. Cardiol., 20:1238–1245, 1992; P. M. Sapin, K. D. Schroder, A. S. Gopal, M. D. Smith, A. N. DeMaria and D. L. King, "Comparison Of Two- And Three-Dimensional Echocardiography With Cineventriculography For Measurement Of Left Ventricular Volume In Patients", J. Am. Coll. Cardiol., 24:1054–1063, 1994; A. S. Gopal, M. J. Schnellbaecher, Z. Shen, O. O. Akinboboye, P. M. Sapin and L. D. King, "Freehand Three-Dimensional Echocardiography For Measurement of Left Ventricular Mass: In Vivo Anatomic Validation Using Explanted Human Hearts", J. Am. Coll. Cardiol., 30:802–810, 1997). Other investigators have also used the spark gap system for calculation of left ventricular volume, mass and for determination of the mitral valve shape. This transducer location technique eliminated the physical connection between the transducer and the reference system thus overcoming some of the restrictions imposed by mechanical transducer location systems. The technique, however, requires a clear line of sight between the transmitting and receiving elements which may not always be feasible. Another disadvantage is that taking tomograms at arbitrary angles may cause unnecessary oversampling of certain regions and under-sampling elsewhere.

Maehle and coworkers (J. Maehle, K. Bjoernstad, S. Aakhus, H. G. Torp and B. A. J. Angelsen, "Three-Dimensional Echocardiography For Quantitative Left Ventricular Wall Motion Analysis: A Method For Reconstruction Of Endocardial Surface And Evaluation Of Regional Dysfunction", *Echocardiography*, 11:397–408, 1994), evaluated rotational acquisition system using only 3 or 4 tomograms acquired in polar coordinate. The rest of the LV contour was restored using spline interpolation. This "triplane" or "quadruplane" approach has expectably proven to be superior over single- or biplane methods. The limited number of views makes this method sensitive to foreshortening of the LV apex and may not be sufficient for reproduction of LVs with complicated shape. This work, however, highlighted the fact that a limited number of tomograms greatly reduces an elaborate outlining of an LV contour while still providing valuable information about its function.

The transesophageal echocardiographic (TEE) technique provided a new window to the heart after its clinical introduction in the 1980's (J. B. Seward, B. K. Khandheria, J. K. Oh, M. D. Abel, B. W. Hughes, W. D. Edwards, B. A. Nichols, W. K. Freeman and A. J. Tajik, "Transesophageal Echocardiography: Technique, Anatomic Correlation, Implementation And Clinical Applications", *Mayo Clin. Proc.*, 63:649–680, 1988). Close proximity of the transducer to the heart allowed uniformly higher quality images than those provided by transthoracic echocardiography. Kuroda, Greenleaf, et al. (T. Kuroda, T. M. Kinter, J. B. Seward, H. Yanagi and J. F. Greenleaf, "Accuracy Of Three-Dimensional Volume Measurement Using Biplane Transesophageal Echocardiographic Probe: In vitro Experiment", *J. Am. Echo.*, 4:475–484, 1991) describe 3D LV reconstruction for morphology and volume assessment using a set of sequential 2D tomographic longitudinal images acquired by rotation of the shaft of a transesophageal probe. Martin et al. (R. W. Martin and G. Bashein, "Measurement Of Stroke Volume With Three-Dimensional Transesophageal Ultrasonic Scanning: Comparison With Thermodilution Measurement", *Anesthesiology*, 70:470–476, 1989; R. W. Martin, G. Bashein M. L. Nessly and F. H. Sheehan, "Methodology For Three-Dimensional Reconstruction Of The Left Ventricle From Transesophageal Echocardiography", *Ultrasound Med. Biol.*, 19:27–38, 1993) have devised an endoscopic micromanipulator for multiplanar transesophageal echocardiographic (TEE) imaging. This system requires a modified transesophageal probe which allows controlled "fan" sweeping with the transducer, thus collecting a pyramidal volume of images. This system capitalizes on an unlimited ultrasound window through the transesophageal access.

Pandian et al. (N. G. Pandian, N. C. Nanda, S. L.

Schwartz, P. Fan, Q. Cao, R. Sanyal, T. Hsu, b. Mumm, H.

Wollschlager, A. Weintraub, "Three-Dimensional And Four-Dimensional Transesophageal Echocardiographic Imaging Of The Heart And Aorta In Humans Using A Computed Tomographic Imaging Probe", Echocardiography 9:677–687, 1992) have evaluated the first commercially available Echo-CT system (Tomtec Imaging Systems, Inc.) for LV function assessment. This PC-based system processes the video signal from an ultrasound scanner and features a model for ECG and respiratory gating. It uses movable holders for TTE probes and a dedicated TEE probe which is made straight and stiff after insertion for an incremental parallel scanning. This system provides dynamic 3D images and can be accommodated to virtually any acquisition geometry and imaging system (N. C. Nanda, R. Sanyal, S. Rosenthal and J. K. Kirklin, "Multiplane Transesophageal Echocardiographic Imaging And Three-Dimensional Reconstruction", *Echocardiography*, 9:667–676, 1992). However, complicated articulation of the TEE probe and rather bulky mechanical adapters for TTE probes make a routine use of this system difficult.

Variable plane (multiplane) transducers have recently been introduced by all major ultrasonic transducer manufacturers (Hewlett Packard, Acuson, Aloca, Toshiba, etc.). A miniature transducer array is mechanically rotated inside the probe tip to acquire successive tomographic views, which combined form a 3D image data set. Typically, both ECG and respiratory gating are used so that each incremental view is acquired during the same phase of the cardiac and respiratory cycles. This requires several minutes to collect a complete 3D data set and it is difficult to keep the patient motionless and the transducer in proper position.

Another factor contributing to extended scan time is the fact that ultrasound cardiac images are prone to noise, signal dropout, and other artifacts. This and an intrinsic variability of biological shapes make it very difficult to identify heart cavity boundaries without an extensive 3D data set which requires a long time to acquire.

A single application of noise removal and edge detection operators, such as those described by Pitas and Venetsanopoulos (I. Pitas and A. N. Venetsanopoulos, "Order Statistics In digital Image Processing", Proceedings of IEEE 80:1892–1921, 1992) results in sparse information about cardiac boundaries. Additional a priori knowledge about LV shape consuming manual delineation.

Coppini et al. (G. Coppini, R. Poli and G. Valli, "Recovery Of The 3-D Shape of The Left Ventricle From Echocardiographic Images", IEEE Transactions On Medical Imaging 14:301–317, 1995) combine conventional edge detection methods and edge grouping through a curvature analysis with a conventional, two-layer neural network, trained on edge position, direction length, angle, and other local parameters to determine which edge was associated with the LV boundary. Subsequently, an elastic, closed surface ellipsoidal model is used to form the endocardial surface by fitting into the recognized edges. Parametrization of the model represents a significant computer load and requires user-guided adjustment of values controlling flexibility and expansion of the model.

Manhaeghe et al. (C. Manhaeghe, I. Lemahieu, D. Vogelaers and F. Colardyn, "Automatic Initial Estimation Of The Left Ventricular Myocardial Midwall In Emission tomograms Using Kohonen Maps", IEEE Transactions on Pattern Analysis and Machine Intelligence 16:259–266, 1994) use self-organizing maps (SOM) to delineate myocardial midwall in emission tomograms. The SOM is an unsupervised neural network technique, introduced by T. Kohonen (T. Kohonen, "Self-Organizing Maps", Springer-Verlag, N.Y., 1995). The SOM consists of nodes that distribute themselves according to intensities in the emission images. Connection of neighboring nodes results in a closed outline of the myocardial midwall.

SUMMARY OF THE INVENTION

The present invention is practiced by rapidly acquiring a 3D image data set using an ultrasonic transducer, processing the 3D image data set to locate a cardiac cavity boundary, and calculate the volume within that cardiac cavity boundary.

One aspect of the invention is the quick acquisition of a 3D data set using a rotating ultrasonic transducer. The quick acquisition of ultrasound tomograms is based on a continuous rotation of the transducer while acquiring serial sectional planes. No gating is employed, however, the cardiac phase is recorded as each serial sectional plane is acquired.

The number of collected images is a product of a time of rotation and a frame rate. For example, a typical 6-second rotation with 30 frames/sec will collect 6×30=180 frames over 180° span, i.e. 1 frame will represent 1° increment which is sufficient for high resolution 3D reconstruction of static structures.

When applied to cardiac imaging the continuous collection of all image frames remains unchanged, but only those frames associated with a particular cardiac cycle phase (i.e. R wave, T wave, etc.) are selected for the 3D image data set. Assuming 80 beats/min. and 6-second rotation, then 8 slices yield gating for one phase. This slice sampling determines lower-resolution (gross-anatomic) 3D reconstruction of a heart and provides data for precise and accurate left ventricular volume measurement. Slower rotation (and thus acquisition longer than 6 seconds) results in more collected frames and, therefore, higher slice resolution, if required. Creation of a series of volumes for several cardiac cycle phases yields four-dimensional (4D) imaging (height, width, depth, time).

Another aspect of the invention is the identification of a cardiac cavity boundary from a limited 3D image data set. A reference database which indicates the likely location of nodes on the cardiac cavity boundary is established by a learning process and during a performing process regions of interest are located in the acquired 3D image data set corresponding to the node locations in the reference database, and the cardiac cavity boundary is located in each region of interest using the 3D image data therein.

A general object of the invention is to acquire 3D ultrasound image data in a short scan time. By continuously rotating the ultrasonic transducer and acquiring tomogram slices at the maximum frame rate an entire 3D image data set can be acquired in seconds. This enables images of moving organs such as the heart to be acquired at many of its phases.

Another object of the invention is to locate cavity boundaries in variable (i.e., lower-resolution or dense) 3D ultrasound image data of typically limited quality (noise, dropouts, etc.). A learning process in which experts identify cavity boundaries in 3D images is used to produce a reference database which indicates regions where the cavity boundary is most likely to be found. This reference database is employed during a performing process to locate the cavity boundary in a 3D image of a patient.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
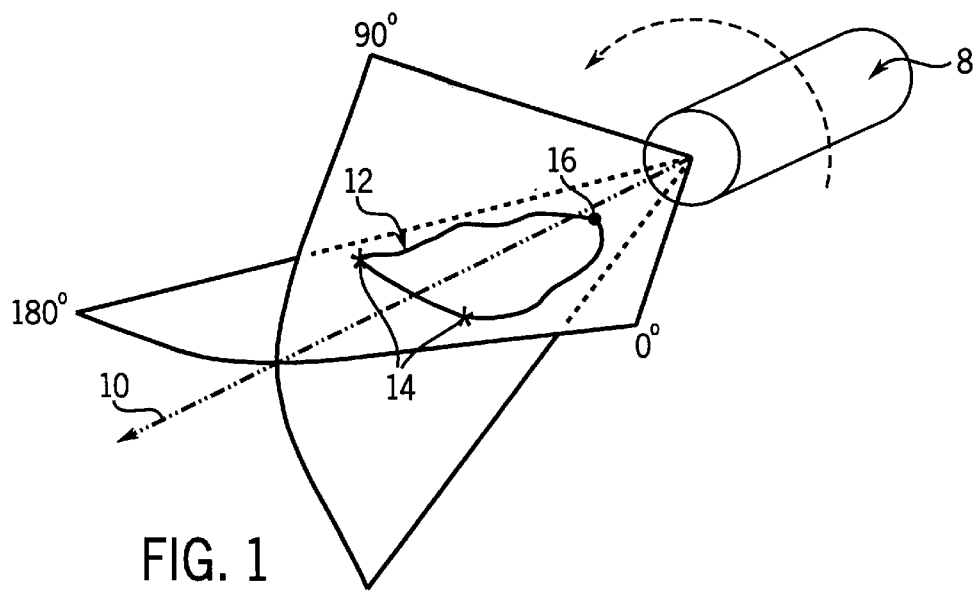
FIG. 1 is a pictorial representation of the imaging planes from which a rotating ultrasonic transducer acquires a 3D image data set according to the preferred embodiment of the invention.

Quick image acquisition is performed with ultrasonic transducer 8 during a clinical study using "propeller" rotational imaging geometry, as shown in FIG. 1. Although other comparable geometry can be used, an important characteristic of the "propeller" geometry is that the slice resolution is unchanged along the imaging axis at the same radial distances. This property makes this technique particularly useful for reconstruction of images of the whole LV. Referring to FIG. 1, the transducer 8 rotates in a 180° arc about its imaging axis 10 acquiring cross-sectional planes through the LV as indicated at 12. These cross-sectional (tomographic) planes form a data set for reconstruction of a 3D image of the LV. The last position of the imaging plane (i.e. 180°) is a mirrored image of the initial position of the imaging plane (i.e. 0°). In the TTE approach, for complete reconstruction of the left ventricle (LV), for example, the points which are located at the cross-section of the MV annulus are indicated at 14. The assumed long axis of the LV is defined by a line extending from the annulus center to an LV apex indicated at 16. This LV long axis may not be parallel to the imaging axis 10 of the transducer 8. The MV hinge and apical points 14 and 16, respectively, in the set of cross-sectional planes determine the spatial orientation of the LV. The commercial availability of a rotatable TTE transducer 8 is anticipated. The same geometry also applies to transducer and a rotatable TEE commercially available from Hewlett Packard and sold under the trademark OMNIPROBE. This transducer has been used in the preferred embodiment.

Using low density rotational geometry, i.e. with as few as three or four slices, yields accurate LV volumes. The validation has been performed in vitro using axially symmetrical latex balloons or mildly asymmetrically deformed balloons with a smooth transition from deformed to intact regions. Under these circumstances, spline interpolation, which has been used to fill the voids between adjacent slices, reproduces the endocardial surface adequately for accurate volumetric results. However, limited surface sampling made this method sensitive to apical foreshortening, and therefore, unsuitable for reproduction of more complicated shapes, and improper for 3D anatomical reconstruction. Additionally, LV boundaries are often incomplete in ultrasound images due to signal attenuation and noise. Checking of data in adjacent reconstructed slices (i.e. 3D mathematical solution) may substitute information for adequate manual or computer-driven delineation of the LV cavity boundary. A large angular span between adjacent slices (i.e. 45° or 60° using four or three slices, respectively) may not provide sufficient sampling along the rotational circumference (i.e. insufficient slice resolution) to approximate missing LV wall anatomy from the previous and subsequent slices.

For a typical size of the papillary muscles or width of the left ventricular outflow tract (LVOT), the circumferential distance between boundary points should not exceed 1–1.5 cm even in a dilated LV. Depiction of 3D anatomy using this level of slice resolution is termed herein as "gross-anatomy imaging". Approximately 6 to 9 tomograms spread over 180° rotation of the transducer 8 are required to yield this circumferential distance from 1.0 to 1.5 cm between adjacent slices in a dilated LV with a short axis diameter of 6 cm. If the dilated LV has a hemiellipsoidal geometry and its long axis is 9 cm, then the circumference of the endocardium in each long-axis tomogram (i.e. the circumference of a hemiellipsis) is approximately 21 cm. This circumference can be divided into 14 to 21 segments to obtain the desired sampling of 1.0 to 1.5 cm. In the preferred embodiment boundary partitioning with 17 nodes into 16 longitudinal segments is done in each long-axis tomogram for endocardial contour mapping.

Constantly rotating transducers have been employed in clinical studies. No reinsertion of the TEE probe or attachment of rotational devices for TTE scanning was necessary. Rotation over 180° took only 6 seconds to complete. This short scan time allowed a repeat of image collection during the course of a routine clinical study to achieve optimal viewing angles. This approach assumes a regular cardiac rhythm, which may not be the case even in a normal subject where the heart rate increases and decreases periodically with quiet inspiration and expiration by approximately 5% (i.e. sinus arrhythmia). These slight irregularities in the cardiac rhythm may cause only barely discernible distortion in the interpolated, gross-anatomical 3D reconstructions.

Only patients with a heart rate equal to or greater than 60 beats/min (bpm) were considered for data acquisition in order to collect at least 6 tomograms for sufficient slice resolution. However, this did not represent an obstacle because most patients have a heart rate above the 60 bpm limit. Rotatable transducers with an adjustable rate of rotation would remove this limitation and are under commercial development by Hewlett Packard and Acuson. Post-priori ECG gating was used to interactively pick appropriate slices. Six-second breathholding was not practical in sedated patients examined by TEE. Thus, respiratory gating was not used and adjacent slices were mutually registered using a cross-correlation method to compensate for transducer motion relative to the heart during the respiratory cycle.

Quick image acquisition using a continuously rotatable transducer 8 is a clinically feasible method of 3D image data collection that offers many advantages. The number of collected tomograms during one sweep is a product of the time of transducer rotation and an acquisition frame rate. The requirement to obtain at least six post priori ECG-gated images can be satisfied in most cases. A slower rotation rate (and thus an acquisition time longer than 6 seconds) allows collection of a sufficient number of tomograms in patients with bradycardia, or it provides higher slice resolution (if required) in patients with a heart rate over 60 bpm. Unlike conventional approaches to serial image acquisition, where the ultrasonic scanning plane is incrementally rotated with respect to pre-determined ECG and respiratory gating limits, the present invention introduces the concept of a quick acquisition using continuous transducer rotation. Distortion of the reconstructed gross anatomy from the resulting lower resolution 3D image data set does not influence LV volume measurement in a statistically detectable manner (i.e. the resulting volumes were precise and accurate). No assumption about heart rate regularity is necessary if the transducer 8 also produces an indication of its angular orientation during rotation.

The rapid continuous acquisition technique actually collects images throughout typically 6–9 complete cardiac cycles over the 6-second period of transducer rotation, assuming a heart rate of 60–90 bpm. This method is thus a source of quickly acquired four-dimensional (4D) data of a beating heart, where the fourth dimension is cardiac phase and each tomographic, cross-sectional plane is acquired while the heart is at a particular phase of its cardiac cycle. The cardiac phase is recorded (using ECG tracing) along with the acquired tomographic images during the 6-second rotational scan of the transducer 8. Thus, 6–9 complete 3D image data sets can be formed, and the data sets represent 6–9 successive cardiac phases. Redundant data along the imaging axis 10 (i.e. at an intersection of the tomographic planes) are averaged, and missing image data (due to drop outs, etc.) for a particular angle and cardiac phase can be interpolated from nearby samples.

The method is also useful for image acquisition from static organs (e.g. abdominal 3D ultrasound, etc.) where a 6-second acquisition at 30 frames/sec with no need for gating results in 6×30=180 collected serial images and thus yields a rapidly-acquired, high resolution 3D image with 1° slice increments.

The second aspect of the invention is a novel approach for analyzing the acquired 3D image data set to accurately define the LV boundary and measure LV cavity volume. The approach includes a new, noise-resistant cardiac boundary detection process, based on order statistics, and a new solution for 3D mapping of a cardiac cavity surface, which makes use of incomplete (i.e. dropout-prone) echocardiographic images. The latter system consists of a unique learning algorithm and a novel 3D application of neural network techniques of self-organization. In the preferred embodiment, the system is applied to the analysis of the LV.

Echocardiographic images can be separated into two classes—the cavity blood pool, characterized by a low mean value of gray, and the myocardium, characterized by a high mean value of gray. Cardiac boundaries are indirectly indicated as the interface between these two classes. This interface, however, may not exactly match endo- and epi-cardium boundaries due to artifacts that are often associated with ultrasound images.

Major artifacts (image dropouts) are caused by signal attenuation or parallel orientation of the beam with respect to the boundary. Conventional edge detectors are sensitive to noise, typically contained in ultrasound images, and produce results with numerous false edges. Complicated recognition methods and user-controlled thresholding methods are then required to pick only those edges that are related to the LV boundary. Various noise-filtering techniques are available, however, they have to be used carefully to prevent or at least minimize deterioration of true edges.

Figure 8:
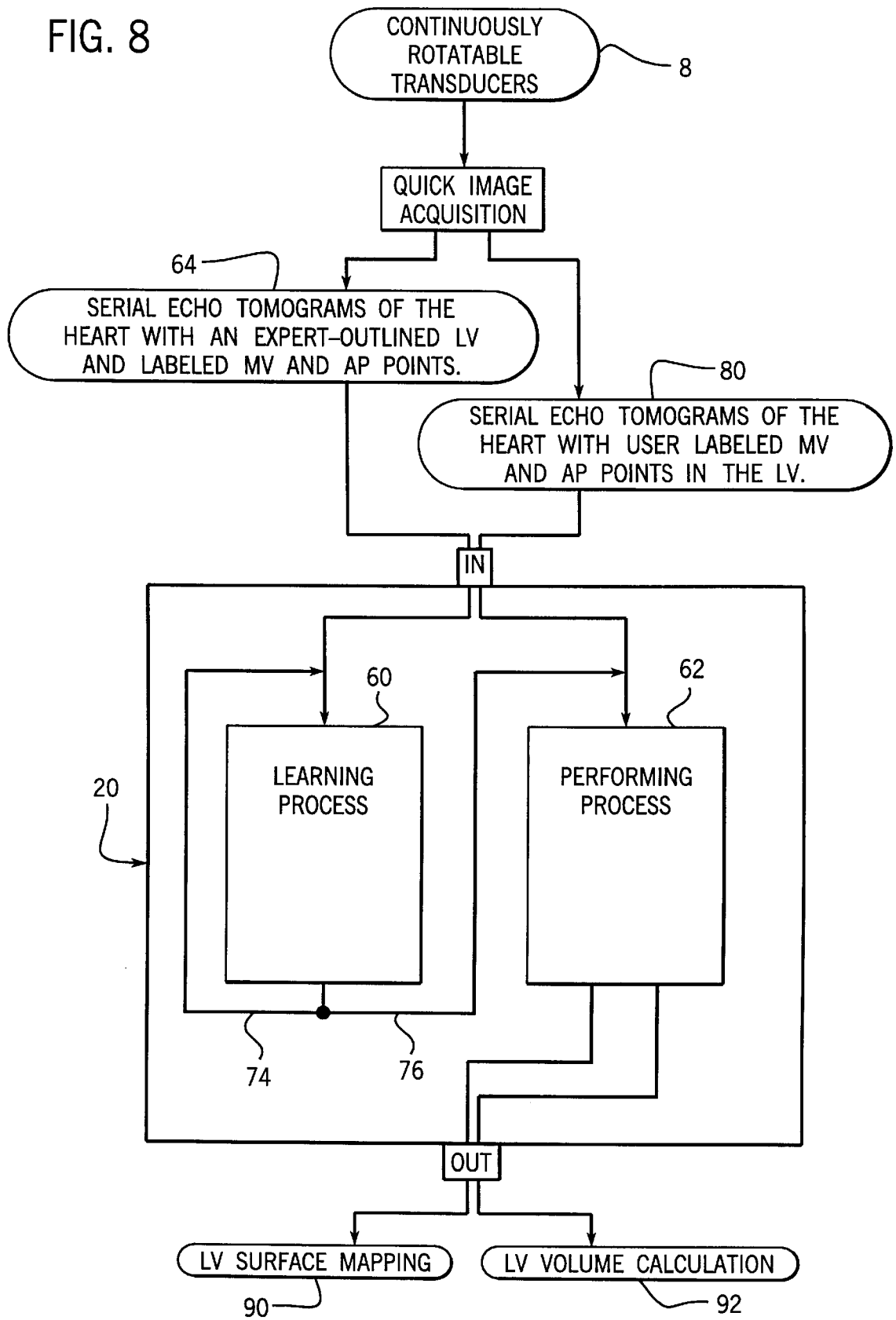
FIG. 8 is a block diagram of the preferred embodiment of the fast cardiac boundary imaging (CBI) system.

A block diagram of the preferred embodiment is shown in FIG. 8. It employs the quick image acquisition technique described above and carried out with the rotatable echocardiographic transducers 8. It also includes a computer cardiac boundary imaging (CBI) system, implemented as a C language program using a commercially available software package (Khoros 1.0, The University of New Mexico, 1992) and a Sun SPARCstation 20. Appendix 1 discloses a user interface as it appears after activation of this code. Appendix 2 discloses a file "CBI.pane" which defines this interface. Appendix 3 discloses a file "CBI.conf" which defines appropriate configuration and library links for the Khoros 1.0 package.

Appendix 4 discloses a file "CBI.prog" which is the complete C code which performs the knowledge-based cardiac boundary imaging system. This code includes appropriate library calls for implementation in Khoros 1.0. The code automatically generates data files ROI_ITER_D and ROI_ITER_S (number of learning iterations for diastolic and systolic contours); ROI_X_D and ROI_X_S (x-coordinates of vectors describing diastolic and systolic contours); and ROI_Y_S and ROI_Y_S (y-coordinates of vectors describing diastolic and systolic contours). The C code includes standard subroutines for spline interpolation (i.e. spin2, splie2, spline, splint), array memory space allocation (i.e. vector, matrix, cube, hypercube) and removal (i.e. free_vector, free_matrix, free_cube, free_hypercube), and a standard error message (i.e. nrerror) published in W. H. Press, B. P. Flannery, S. A. Teukolsky, and W. T. Vetterling, "Numerical Recipes in c. The Art of Scientific Computing", Cambridge University Press, New York, N.Y., 1989. The source code in Appendix 4 contains explanatory notes and process block numbers which are used in the following description of the preferred embodiment of the invention.

Figure 3:
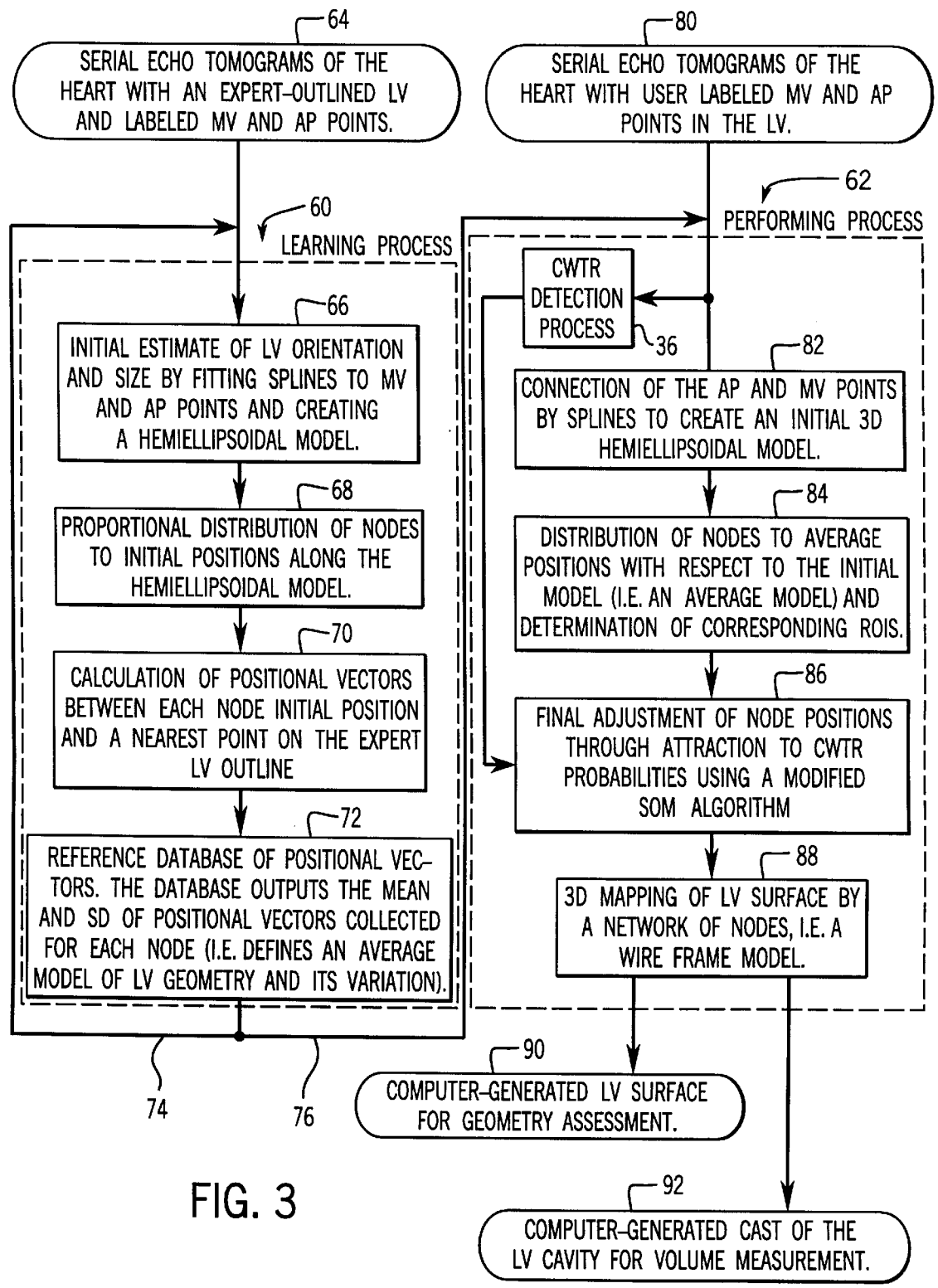
FIG. 3 is a flow chart of a program which carries out the learning process and the performing process of the present invention.

The cardiac cavity boundary imaging system of the present invention includes a "learning" process 60 and a "performing" process 62. The flow chart for these two processes is shown in FIG. 3. The learning process 60 requires as input at process block 64 a set of serial echo tomograms with expert outlines of the endocardium and with labeled apical (AP) and mitral valve MV hinge points 16 and 14, respectively. Clinical tomograms must be collected consistently, starting with a four-chamber long-axis image and rotating in a counter-clockwise direction (when looking at a TEE transducer face) or clockwise direction (when looking at a TTE transducer face). A preprocessing step is required to normalize gray scale levels (in 8-bit images used in the preferred embodiment) to a range from 1 to 250. An echocardiography expert defines the MV and AP points 14 and 16, respectively, using 1×1 pixel labels, as well as the endocardium outline in each tomogram. The pixel labels and the outline must be of unique intensity values other than 1 to zero.

Figure 4:
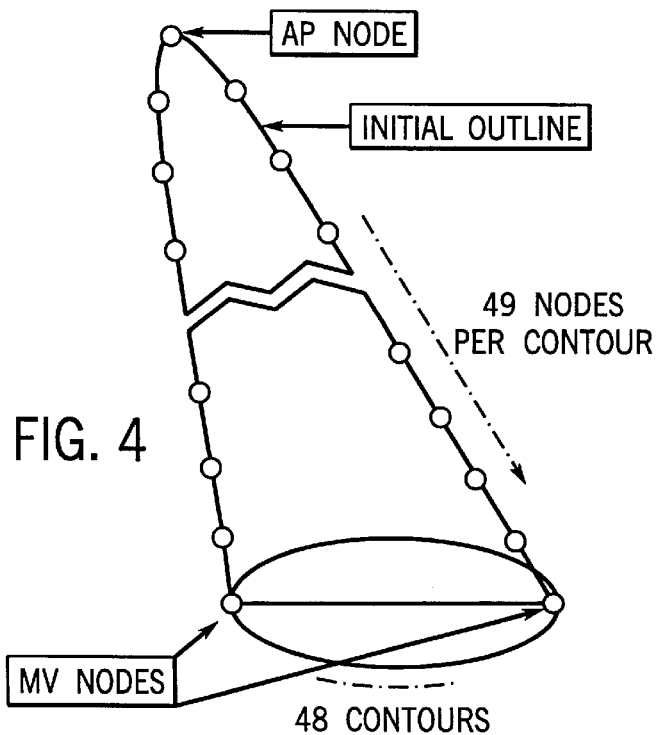
FIG. 4 is a schematic representation of the scheme of initial node placement on one out of 48 hemielliptic contours that form the initial hemiellipsoid, individual nodes are distributed proportionally along each contour, and assignment of mitral and apical nodes supports spatial orientation of the generated hemiellipsoid.

The learning process generates an initial estimate of LV size and geometry at process blocks 66 and 68 by fitting a deformable hemiellipsoid (represented by proportionally distributed nodes) into the identified AP and MV points 16 and 14, respectively, in each echotomogram of the set. As shown in FIG. 4, a spline, that starts at one of the MV points 14, continues through the AP point 16 and ends at the other MV point 14, is generated in each slice thus creating initial hemielliptical contours. Contours produced from all tomograms form a hemiellipsoid which fits into the MV and AP points 14 and 16. A total of 48 hemielliptical contours are generated for a 3D data set, but because only 6–9 outlined tomograms typically compose the patient cardiac 3D scan, the intermediate contours are generated using bicubic spline interpolation. Subsequently, 49 nodes 17 are distributed proportionally along each contour and thus placed in initial positions to divide the contour into 48 partitions. The first and last (49th) nodes are called the MV nodes 14, because they match the MV point positions, and the middle (25th) node is called the AP node 16. This completes an initial estimate of the LV cavity boundary surface by a hemiellipsoidal model based only on the MV and AP points 14 and 16 labeled by the expert user in all component tomograms. This is referred to herein as the "initial LV estimate".

Figure 5:
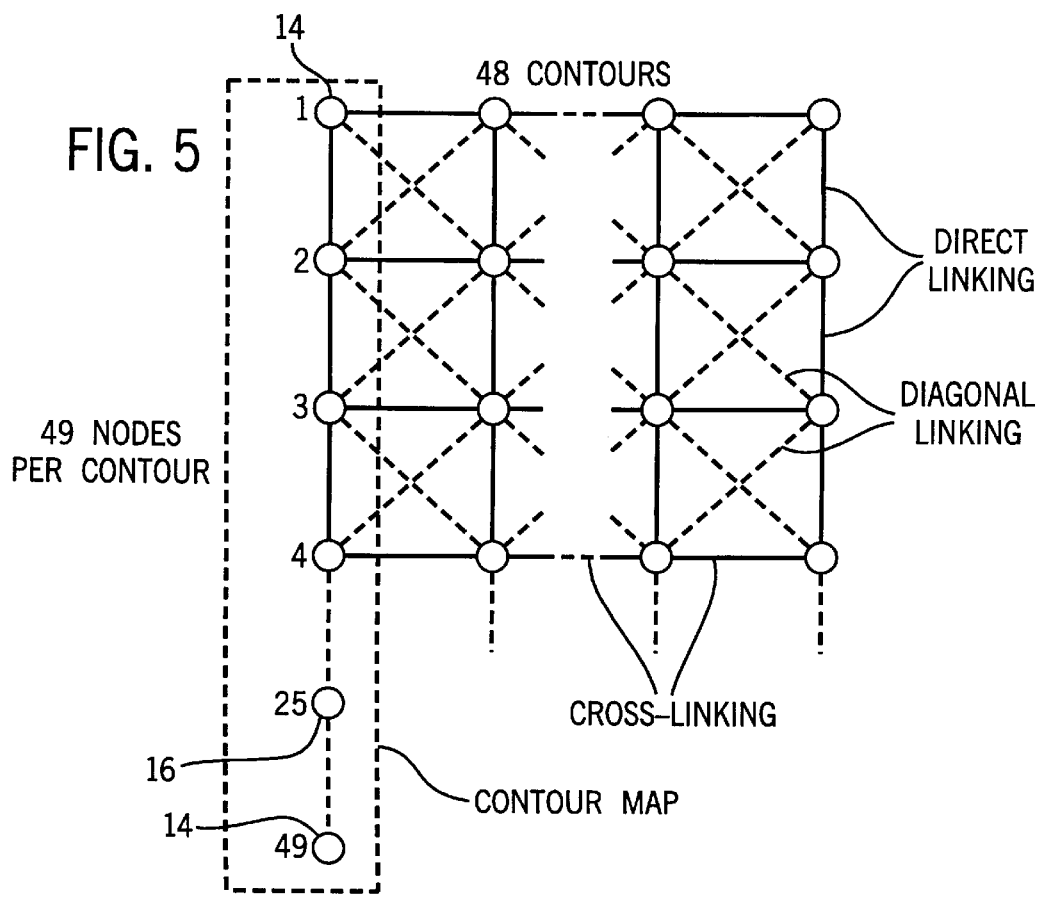
FIG. 5 is a schematic drawing of nodes mapped onto a rectangular lattice which defines their neighborhood relationships in which direct linking represents neighborhoods along the endocardial circumference within a slice, cross-linking connects neighborhoods across adjacent slices, and diagonal linking is a neighborhood connection to a neighbor of the node bridge by a cross-link.

As shown in FIG. 5, the design with 48 contours and 49 nodes per contour provides a framework for node mapping into a 2D lattice with 48×49=2352 elements. This mapping represents a standard database for description of LV geometry and its variations. No matter how many serial tomograms are actually collected during the learning process 60, they are consistently interpolated into a 48×49 lattice of nodes.

Figure 6:
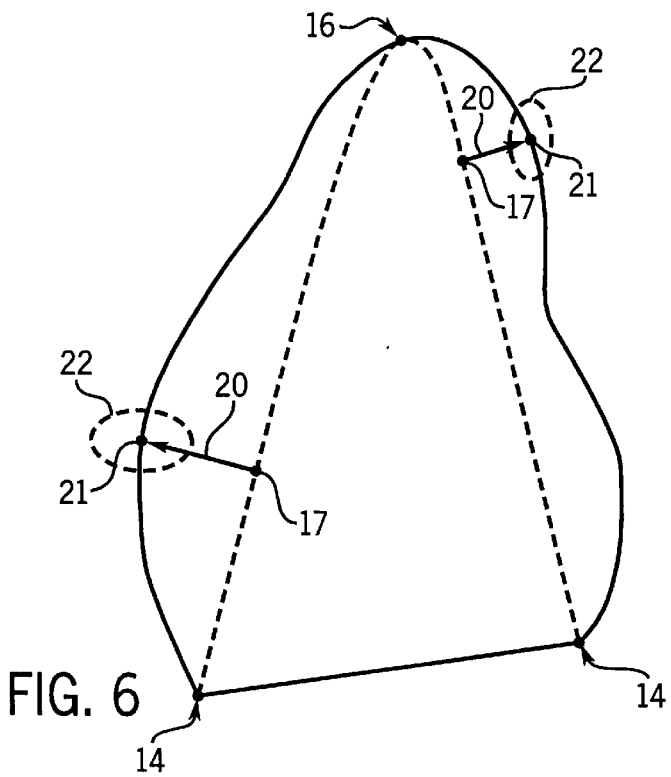
FIG. 6 is a schematic representation of how the average node position is defined by a mean vector between an initial node position and the nearest point on an expert outline.

A positional vector between each node of the hemiellipsoidal model and the nearest point on the echotomogram outline is calculated at process block 70. As shown in FIG. 6, a positional vector 20 from the initial node location 17 in an initial LV estimate to the nearest point of the expert LV outline is calculated for each node 17 in the data set. This is repeated using various, expert-outlined, serial LV tomograms. The resulting mean value of the vector 20 defines an average node position 21. A two standard deviation (SD) range around the average node position 21 defines an ROI where a search for the LV boundary in the acquired image data begins. Individual ROIs 22 may topologically overlap, but are treated separately by the system. The size of the individual ROIs 22 shows the degree of probable variation of LV geometry at each particular average node location based on the knowledge embodied in the expert LV outlines. This way the system creates a priori knowledge about plausible LV geometry (i.e. an average LV model) and its variation.

The average LV model is defined by vectors in a "reference" database 72. The vectors can be recalled by the performing process 62, as diagrammatically shown by link 76. The reference database 72 of node position vectors is generated by the learning process 60 during its first activation and is expanded by new vector measurements whenever a new expert outline is input. The latter is indicated by loop 74. The database has been designed with the following dimensions ($D_i$):

$D_1$—standardized number of 48 outlines;
$D_2$—standardized number of 49 nodes per outlines;
$D_3$—number of examined phases, currently 2 (i.e. diastole and systole);
$D_4$—number of learning iterations per node at a particular phase, (i.e. number of patient data sets used for learning).

The reference database 72 contains original positional vectors and it outputs these through link 76 along with their mean and 2SD values whenever requested by the performing process 62. Thus, for example, 51,744 positional vectors are stored for the standard number of 2352 nodes and 2 phases after 11 learning iterations. These data allow description of average LV diastolic and systolic geometry in 3D, yet result in a very small memory load.

The positional vectors in reference database 72 do not define LV shape directly. Rather, they provide plausible spatial constraints in which the LV cavity boundary should exist with respect to an initial estimate of LV geometry. The spatial constraints are expressed as the ROI 22 around each individual average node position 21. As will be described below, the initial estimate is (similarly to the learning process 60) carried out also during the performing process 62 by fitting splines through MV and AP points 14 and 16 in patient tomograms, thus creating the initial 3D hemiellipsoidal model. This assures compatibility between the learning and performing processes and gives the system the desired flexibility to deal with various LV sizes and geometries. Naturally, computer knowledge and the resulting performance can be only as good as the preceding learning process 60. Separate reference databases 72 may be required not only for diastolic and systolic geometries, but also for intermediate phases or for various clinical pathologic entities.

In the performing process 62, serial tomograms acquired from a patient with user-labeled apical and mitral points are input at block 80. The user manually identifies the apical and mitral points 16 and 14 in each image using a cursor. This initial user interaction is the only manual input in an otherwise automatic LV cavity boundary detection process. The performing process 62 employs (through the link 76) the reference database 72 to locate the LV boundary in these patient 3D image sets.

Figure 2:
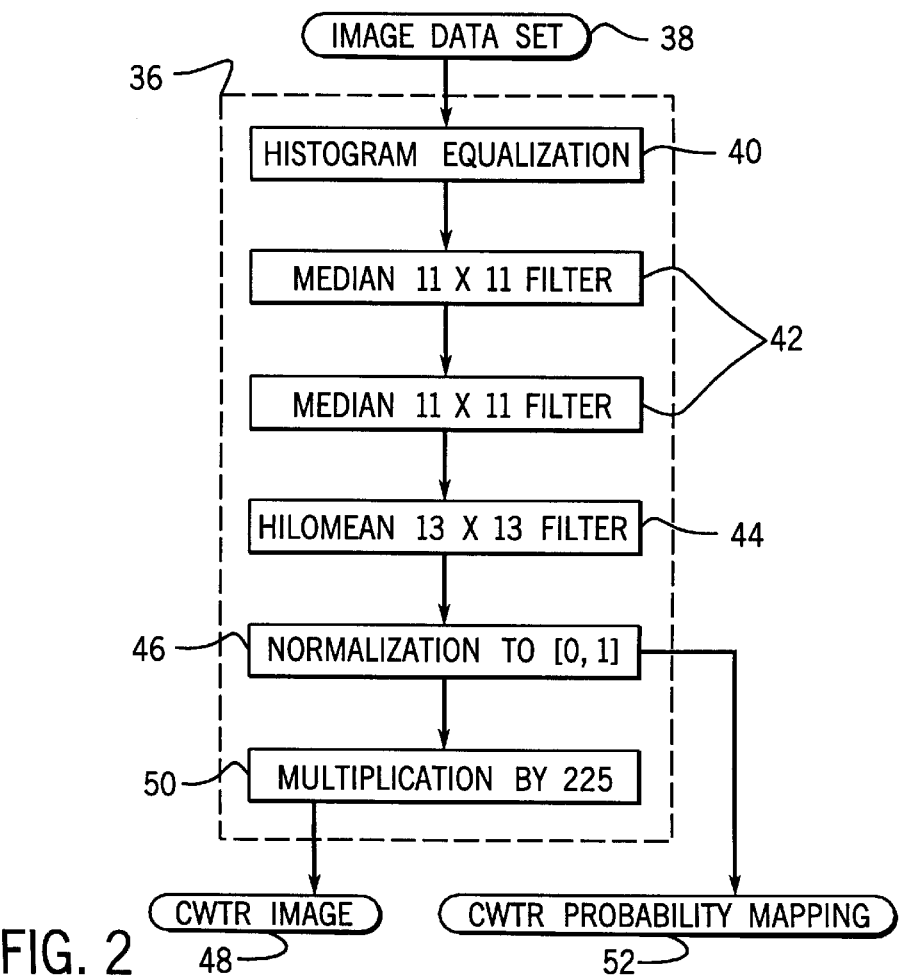
FIG. 2 is a flow chart of a program that assigns to each image pixel a probability of a presence of a cardiac boundary (a CWTR detector) used in the preferred embodiment of the invention.

In the preferred embodiment a cavity-to-wall transition region ("CWTR") detection process 36 is used on the acquired 3D image data set 38 in the performing process 62. This detection process is illustrated by the flow chart in FIG. 2 which will now be described. Histogram equalization of the 3D image data set 38 is performed first at process block 40, followed by two iterations of a median filter to suppress impulsive noise indicated at process block 42. This is followed by a so called "HiLomean" filter indicated at process block 44, the output of which is normalized at process block 46 to translate its output intensity values into probabilities between 0 and 1 (i.e. CWTR probability mapping). A CWTR image 48 is also produced by multiplying the probability at each pixel by 255 as indicated at process block 50. The CWTR image indicates location of boundaries visually by high intensity bands.

The "HiLomean" filter 44 used in the preferred embodiment is an important element of the boundary detection process and will now be described in detail.

In general, a rank ordered mean filter can be defined as follows:

$$y_i = \sum_{j=1}^{\beta n} \frac{1}{\beta n} x_{(j)} \quad (1)$$

where $\beta$ ($0 < \beta \leq 1$) defines the selected rank in the ordered input values $x_{(j)}$ and n is a number of pixels in a filter window. Assuming that transition from black to white corresponds to a numerical transition from 0 to 255 in an 8-bit gray scale image, the filter defined by equation (1) can produce a mean value biased towards the lowest intensities (i.e. darkest pixel values) and has been termed the "Lomean" filter. Its operation is adjusted through a parameter $\beta$: the setting of $\beta$ close to 0 will result in a significant bias to lowest intensities, the setting of $\beta = 1$ will result in the conventional mean filter.

Consequently, the filter $$y_i = \sum_{j=1}^{n(1-\beta)+1} \frac{1}{\beta n} x_{(j)} \quad (2)$$

can bias the mean towards high intensities as it sums the ordered input values $x_{(j)}$ in the descending direction. This filter is called a "Himean" filter. Setting $\beta$ close to 0 will match the maximal bias, and setting $\beta = 1$ will, similarly to the Lomean filter, result in conventional mean filter performance.

Taking the absolute value of the difference between Himean and Lomean values calculated in accordance with equations 1) and 2) results in a function, proportional to the probability of the presence of the CWTR. The filter 44 that calculates this function has been termed "HiLomean" filter and is defined as follows:

$$y_i = \left| \sum_{j=n}^{n(1-\beta)+1} \frac{1}{\beta n} x_{(j)} - \sum_{j=1}^{\beta n} \frac{1}{\beta n} x_{(j)} \right| = \frac{1}{\beta n} \left| \sum_{j=n}^{n(1-\beta)+1} x_{(j)} - \sum_{j=1}^{\beta n} x_{(j)} \right|. \quad (3)$$

In the preferred embodiment, an n=m×m filter window has been employed and the continuous scale of $\beta n$ values has been replaced by discrete ranking characterizing the number of ordered pixel intensities within the m×m window used in the HiLomean filter. The 0th rank means that only the lowest and highest pixel intensity values were included for filter operation; the 1st rank means that 1×m lowest and highest pixel intensity values were taken; the 2nd rank means that 2×m lowest and highest intensities were considered, etc. For particular noise conditions, the lowest possible rank should be used to obtain a maximum dynamic range of the resulting values. The minimal configuration of the HiLomean filter 44 includes the use of a 9×9 pixel window. Preprocessing by at least one iteration of a 9×9 median filter prevents the blotchy appearance of the resulting images, typical for filters based on ranking of local pixel intensities. The combination of the HiLomean filter 44 with the median filter 42 and other supporting image operations (i.e. histogram equalization 40 and gray scale normalization 46) forms the CWTR detector 36.

Tests performed on average or suboptimal quality clinical echocardiographic images demonstrate that noise resistance and edge preservation is optimal using a 1st rank of ordered values and a window size between 9×9 and 17×17 pixels (for 1 pixel=0.342 to 0.457 mm calibration). The preferred configuration of the CWTR detector 36 uses a 13×13 window (i.e. a compromise between 9×9 and 17×17 pixel size).

The performing process 62 first fits an initial hemiellipsoidal model into the identified AP and MV points 14 and 16 as indicated at process block 82. This is the same step used in the learning process 60 in block 66 to produce automatically an initial outline of the LV endocardial boundary using spline interpolation through AP and MV points in each tomogram. Because of limited initial input data (i.e. only 3 points in each tomogram), the resulting contour represents a greatly generalized (hemiellipsoidal) reproduction of an LV cavity and would typically underestimate its volume, especially in asymmetrically enlarged LVs. The model provides, however, a foundation for node distribution in a 3D space with respect to LV size and orientation as revealed by the AP and MV points 14 and 16.

The next step in the performing process 62 is to distribute nodes to average positions with respect to the initial model as indicated at process block 84. This is also analogous to the learning process 60 described above. As indicated, 17 nodes are sufficient to define an LV cavity boundary in each long-axis tomogram. During learning about LV geometry, the system internally describes the boundary through the standardized database 72 with 49 nodes per slice. This number of nodes assures a reserve for future higher spatial resolution imaging. In the performing mode, however, the average position of each of 17 nodes and the size of the corresponding ROI for each node are derived from the reference database 72. Neighboring nodes are interconnected by splines. This completes generation of a 3D "average model" of the LV cavity boundary in an examined 3D data set.

In other words, automatic relocation of nodes to their "average" positions with respect to the initial model in the patient 3D data set utilizes previously gained knowledge (from experts) about a plausible LV cavity boundary shape. Location of nodes in the 3D image set and the ROI associated with each node provide information where to search for the cavity boundary of the LV, thus avoiding confusion by other cardiac boundaries and image artifacts. This point is critical for understanding the unique functioning of the system: it first learns from experts (process 60) how an LV may look like and then it uses this a priori knowledge to define a plausible variation of LV boundary location in a previously unseen patient 3D image set. This simulates the human expert process of learning and then applying the learned experience to a new situation.

The tomographic data acquired from the patient are also processed through the CWTR detector 36 to create a CWTR probability map 52. Pixel intensities in this CWTR map represent the probability of a presence of the transition region between the LV cavity and the LV wall, i.e. the probability of a presence of the cavity boundary. Automatic placement of nodes in the average outline and assignment of corresponding ROIs defined in the reference database 72 restricts this process to the endocardial region. Selectivity of individual ROIs with respect to the endocardium depends on local variability of LV shape and wall thickness in images used during the prior development of the reference database 72 (i.e. during the learning process). Construction of an initial hemiellipsoidal model, calculation of average node positions with respect to this model, and determination of corresponding ROIs represent a main pathway in the performing process 62. The CWTR detector 36 is activated independently and the resulting CWTR probability mapping is combined with the ROIs in block 86.

A modified self-organizing map (SOM) algorithm, which is implemented in block 86 as a part of the performing process 62 is responsible for a final adjustment of node positions so that they optimally fit into the CWTR. This multi-iterative procedure relocates each node from its average position in the center of the associated ROI towards a location within the ROI that represents the highest intensity values in the CWTR image. Starting with an average LV model, it forms a final LV model. This process respects node spatial neighborhood relationships. This means that each node may eventually not match the highest local CWTR probability in its ROI. This "cost-minimizing" process is elaborated on in the following paragraphs.

If the SOM algorithm were executed directly on CWTR images (without masking through the use of the ROIs as taught by the present invention), the nodes would be spread all over the image to represent distribution of pixel intensities. If the nodes were initially grouped at one spot or placed randomly, as is typically done when using the "classical" SOM algorithm, many iterations of SOM training would be required to distribute the nodes closely to the target contour. Far fewer iterations are required by the present invention to achieve the same degree of certainty because the process is limited to placing nodes in the ROIs from the reference database 72. The method according to the present invention thus changes the classic SOM algorithm in the following ways:

1) Introduction of a priori knowledge about LV geometry. This knowledge is gained during the learning process 60 and this knowledge is used to place nodes at their average positions. Thus, the distribution of nodes corresponds to LV orientation in 3D space, plausible geometry and size from the start of the SOM algorithm. This modification increases the speed of the algorithm and relates individual nodes to local anatomy. This is important for anticipated studies on regional wall motion abnormalities.

2) Restriction of each node to a ROI that represents local variation of LV geometry learned from real LV images during the learning process 60. The nodes are allowed to move freely only within their corresponding ROIs. This prevents an escape of nodes beyond the LV region and allows a logical LV outline to be produced when boundary definition by the acquired image data is suboptimal.

3) During self-organization, only immediate neighbors in 3D space are considered for position adjustment simultaneously with the winning node in the preferred embodiment (there are eight immediate neighbors mapped on a 2D lattice). This is because with typical angular increments $\theta=22.50$ between echocardiographic tomograms (180°, 8 collected tomograms, 180/8=22.5), the neighbors beyond the immediate ones are unlikely to be anatomically related. The winning node is the one which is to be moved by a fractional distance to a point randomly selected within the associated ROI by an iterative self-organization process. The fractional distance is controlled by a learning parameter $\alpha$ and is set to $\alpha=0.3$ in the preferred embodiment, based on previous optimization tests. Setting of $\alpha$ is not critical as it affects mostly the rate of approach of a node to its final position and lessly the smoothness of the resulting contour. The parameter $\alpha$ approaches zero during the course of finite number of self-organizing process iterations, also called "training cycles."

4) Fractional adjustment of neighboring node positions is controlled, besides the learning parameter $\alpha$, also by a function of $\cos\theta$ which represents a vector component of the winning node motion and effectively decreases translation of nodes in neighboring slices (i.e. in the elevation direction). Theoretically, for biplane imaging, where $\theta=90°$, there would be no adjustment of neighbors across the tomograms (no matter how much the winning node moved) because $\cos 90°=0$. Neighbors beyond the 90° angular distance are not considered for adjustment at all. Analogous rules apply to nodes within each tomogram (i.e. in azimuthal direction).

The modified SOM algorithm is used to perform final delineation of the LV boundary. This is accomplished through iterative spatial redistributing (organizing) of winning nodes according to their attraction to the CWTR. The SOM algorithm represents a tool for minimization of a total cost of antagonistically acting shaping and smoothing effects. The shaping effect is caused by attraction of winning nodes to areas with highest CWTR values. The smoothing effect relays this transition to neighboring nodes and results in adjustment of their positions too. Other "cost-minimizing" algorithms, such as active contour models (balloons, snakes) and parametrically deformable models could be used too, presumably with similar results but at a price of subjective adjustments of various parameters controlling their functioning.

Final fitting of the generated contour is accomplished in the preferred embodiment after 300 SOM training cycles are applied to each ROI. Thus, for final adjustment of 17 nodes (and the same number of ROIs) in 8 slices, a total of 17×8×300=40,800 training cycles are required. This requires approximately 2 minutes using the Sun SPARCstation 20.

Figure 7:
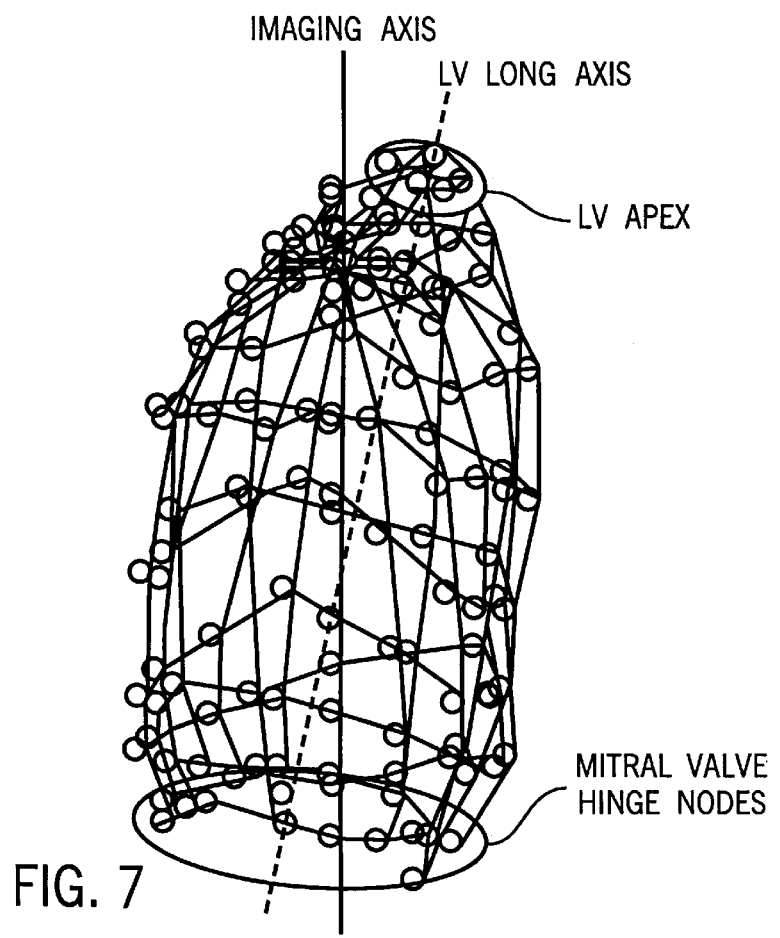
FIG. 7 is a pictoral view which demonstrates mapping of a left ventricular endocardial surface as it can be obtained from a patient using quick echocardiographic image acquisition and the performing process of the present invention.

This iterative process takes into account not only the attraction to the CWTR (as the points with higher CWTR detector output values have proportionally higher changes to be presented). It also evaluates mutual neighborhood relationships of nodes in 3D space (i.e. adjustment of a node position causes some positional adjustment of its neighbors). All nodes are eventually connected using bicubic spline interpolation thus forming at process block 88 a 3D spatial network of nodes which form a "wire frame" model as shown in FIG. 7.

LV cavity boundary recovery by the knowledge-based system is not completely automatic, although the operator involvement is minimal. The performing process 62 requires interactive manual definition of the AP and MV points 16 and 14 in each serial tomogram. Assuming a typical number of 8 tomograms, 24 points have to be labeled which requires about 1–2 minutes. From here, the system works automatically. Average node positions are determined using a priori knowledge in the stored system data base 72 gained during the process of learning, and a final adjustment of node position within a corresponding ROI is carried out over a course of tens of thousands iterations. The automatic process thus greatly minimizes the user interaction and the consequent influence of subjective manual choices made by the user.

The novelty of the knowledge-based system is not only in its ability to learn about a plausible LV geometry and its variation, but also in practical utilization of 3D spatial relationships of individual nodes for parametrization of the LV endocardial surface. It should be kept in mind that the nodes are interrelated not only within each tomogram but also across tomograms. Any positional change of a node is reflected by positional adjustment of its spatial neighbors in adjacent tomograms. If a node is associated with a noise region or an image dropout, and there is little or no clue for its final placement, its position may be derived from the spatial location of its neighbors.

An LV cavity surface acquired with 22.5° increments (8 rotational tomograms) is mapped to the lattice of nodes (FIG. 5) representing 3.75° increments (48 contours). During the learning process 60, this mapping represents organization of nodes into a reference database 72. During the performing process 62, all stages of endocardial boundary detection and formation (i.e. initial, average and final models), discussed above are generated within the frame of this lattice to assure compatibility with the reference database 72. The lattice demonstrated in FIG. 5 also establishes direct, cross, and diagonal linking (neighborhood relationships) used during the final adjustment of node positions by self-organizing process in process block 86. Spline interpolation and vector component (of a node positional adjustment) calculation are employed because spatial resolution represented by the lattice is substantially higher than that of the acquired data. A reverse process (from 3.570 to 22.5° slice resolution) is applied to place nodes and generate LV boundary outlines in original slices in the end of the performing process in block 88.

A novel knowledge-based system for delineation of the LV cavity boundary from sparse and noise-prone data has been described. System operation requires only minimal initial user interaction. The system consists of a unique statistical learning process about LV geometry and its variation and a novel performing process for automatic distribution of nodes that represent the LV endocardial surface in 3D. The two processes 60 and 62 are combined with quick image acquisition and automatic CWTR detection. The system has been applied to ultrasound images of the LV and acts as a trainable "computer expert" for delineation of endocardial boundaries and LV volume calculation. Other applications are possible, since the system can be used for surface mapping of any hollow object which on average maintains some general shape that can be represented by an initial model. The actual object can then be parametrized through differences from the initial model. The differences are described by vectors and stored in a standardized reference database 72. A major advantage of this invention is that a great deal of geometrical variability is covered by adaptation of the initial model, parametrized through node positions. Closer fitting is accomplished by relocating the nodes to their average positions with respect to the model which is based upon knowledge gained through the learning process 60. Final fitting is achieved by node position adjustment to regions with the highest probability of the presence of the endocardium (i.e. the CWTR detector) using a cost minimizing function, represented in the preferred embodiment by a modified, unsupervised neural network process (i.e. SOM). This three-stage process (i.e. initial model→average model→final fitting) is potentially also applicable to LV epicardial boundary detection, and boundary detection and volumetry of the right ventricle, and other generally ellipsoidal (or hemiellipsoidal) organ cavities.

Both learning and performing processes are associated with a special reference database 72 that accumulates data about 3D geometry of the subject and stores them in a standardized format. The reference database 72 is capable of handling different angular increments during the learning and performing modes. This is potentially useful for 3D acquisition and resulting reconstruction with various slice resolutions, even within a single image volume.

The 3D design of the system supports corrected identification of LV cavity boundary by bridging gaps through neighborhood linking of nodes in ultrasound images with dropouts and high levels of noise. Reproduction of LV surface from a multi-tomographic data set, where nodes used for surface mapping are mutually interconnected, yields an averaging (smoothing) effect, particularly desirable in the apical region with a high sampling density. Unlike single or biplane approaches, the 3D nature of the system avoids the need for assumptions about LV shapes.

APPENDIX 1

| Input Image | ^ |
|---|---|
| Output Image | ^ |

- Cardiac phase: diastole
- ROI learning mode: no --v
- Delineation color: 255^
- AP/MV point color: 254^
- Cycles/node: 300^
- 2D neighbors: 1^
- 3D neighbors: 1^
- Low alpha: 0.100000^
- High alpha: 0.300000^

-continued

APPENDIX 1

■ SOM algorithm:   ■ classic     ■ No. of nodes:  ☐ 09  ☐ 33
                   ■ modified                     ■ 17  ☐ 41
                                                  ☐ 25  ☐ 49

■ Output outline  (spline)   ■ Window size:  ☐ 09  ☐ 17
                                             ■ 13  ☐ 25

■ Print node coord.   ■ no
                      ☐ yes-averaged apex
                      ☐ yes-outlined apex

APPENDIX 2

-F 4.2 1 0 1 70×7+10+20 +35+1 'CANTATA Visual Programming Environment for the KHOROS System' cantata
-M 1 1 100×40+10+20 +23+1 'CBI' subform1
-P 1 0 80×38+22++0+0 'Automated Cardiac Boundary Imaging' CBI
-I 1 0 0 1 0 0 50×1+2+2 +0+0 '"Input Image"image in a propeller-like format'
i
-O 1 0 0 1 0 0 50×1+2+3 +0+0 '"Output Image"resulting output image with the SOM superimposed' o
-l 1 0 1 1 0 50×1+2+5 +0+0 0 'Cardiac phase   "diastole' 'systole' 'select diastolic or systolic phase' phase
-i 1 0 1 1 0 24×1+36+6 +0+0 251 255 255 'Delineation color' 'value of an LV outline' delinclr
-l 1 0 1 1 0 30×1+2+6 +0+0 0 'ROI learning mode''no --v ' 'yes -->' 'learn about the ROI from expert outlines' roilrn
-i 1 0 1 1 0 24×1+36+7 +0+0 251 255 254 'AP/MV point color' 'value of AP and MV points' pointclr
-i 1 0 1 1 0 28×1+2+8 +0+0 2 2 300 'Cycles/node' 'no. of training cycles per one node' rep
-i 1 0 1 1 0 28×1+2+9 +0+0 1 1 1 '2D neighbors''number of neighbors within a slice' neigh2d
-i 1 0 1 1 0 28×1+2+10 +0+0 1 1 1 '3D neighbors''number of neighbors across slices' neigh3d
-f 1 0 1 1 0 60×1+2+12 +0+0 0 1 0.1 'Low alpha   ''value of the training parameter alpha'l_alpha
-f 1 0 1 1 0 60×1+2+13 +0+0 0 1 0.3 'High alpha   ''value of the training parameter alpha'h_alpha
-T 1 0 1 1 0 40×1+2+15 +0+0 1 'SOM algorithm:''SOM algorithm selection' algor
-i 1 0 1 1 0 1×1+18+1 +0+0 0 1 1 'modified''modified algorithm' alg
-i 1 0 1 0 0 1×1+18+0 +0+0 0 1 0 'classic''classical algorithm' alg
-E
-T 1 0 1 1 0 50×1+36+15 +0+0 5 'No. of nodes:''number of BCI nodes in one slice' nnod
-i 1 0 1 0 0 1×1+24+2 +0+0 9 49 49 '49''number of nodes' n
-i 1 0 1 0 0 1×1+24+1 +0+0 9 49 41 '41''number of nodes' n
-i 1 0 1 0 0 1×1+24+0 +0+0 9 49 33 '33''number of nodes' n
-i 1 0 1 0 0 1×1+16+2 +0+0 9 49 25 '25''number of nodes' n
-i 1 0 1 0 0 1×1+16+1 +0+0 9 49 17 '17''number of nodes' n
-i 1 0 1 0 0 1×1+16+0 +0+0 9 49 9 '09''number of nodes' n
-E
-l 1 0 1 1 0 30×1+2+19 +0+0 1 'Output outline' 'linear' 'spline' 'Delineation of nodes using lines or splines' delinitp
-T 1 0 1 1 0 50×1+36+19 +0+0 3 'Window size:' 'window size for feature calculation' ws
-i 1 0 1 0 0 1×1+24+1 +0+0 9 25 25 '25''window size' m
-i 1 0 1 0 0 1×1+24+0 +0+0 9 25 17 '17''window size' m
-i 1 0 1 0 0 1×1+16+1 +0+0 9 25 13 '13''window size' m
-i 1 0 1 0 0 1×1+16+0 +0+0 9 25 9 '09''window size' m
-E
-T 1 0 1 1 0 50×1+2+21 +0+0 3 'Print node coord.''prints node xyz coordinate triplets for xprizm3 plot' coord
-i 1 0 1 0 0 1×1+20+2 +0+0 0 2 2 'yes - outlined apex''apex as outlined' o
-i 1 0 1 0 0 1×1+20+1 +0+0 0 2 1 'yes - averaged apex''apex averaged' o
-i 1 0 1 0 0 1×1+20+0 +0+0 0 2 0 'no       ''no printout' o
-E
-R 1 0 1 13×2+2+25 'Execute''do operation' cmdtool CBI
-H   1    13 ×2+49+25   'Help'   'documentation  for   CBI'
$MAREK_TOOLBOX/doc/manpages/CBI.1

APPENDIX 2-continued

-E
-E
-E

APPENDIX 3

/* CBI.conf */
cfile: $MAREK_TOOLBOX/src/som
hfile: $MEREK_TOOLBOX/src/som
lfile: $MEREK_TOOLBOX/src/Lib
man1file: $MEREK_TOOLBOX/man/man1
man3file: $MEREK_TOOLBOX/man/man3

APPENDIX 3-continued progfile: $MEREK_TOOLBOX/src/som
panefile: $MEREK_TOOLBOX/repos/cantata/subforms
helpfile: $MEREK_TOOLBOX/doc/manpages
subhelpfile: $MEREK_TOOLBOX/repos/cantata/subforms
topsrc: $MEREK_TOOLBOX/src

APPENDIX 4

-short_prog_description
This is a practical realization of the Cardiac Boundary Imaging (CBI) algorithm. Khoros ™ software package (Khoros 1.0, The University of New Mexico) and Sun SPARC workstation have been used for implementation of the source C language code. Provided with this 'CBI.prog' file are also 'CBI.pane' and 'CBI.conf' files that define user interface and appropriate configuration within the Khoros 1.0 package, respectively. Using the same version of Khoros and apropriate hardware platform allows immediate implementation of the CBI system. The code is original except for standard subroutines which include spline interpolation (i.e. splin2, splie2, spline, splint), array memory space allocation (i.e. vector, matrix, cube, hypercube) and removal (i.e. free_vector, free_matrix, free _cube, free_hypercube), and a standard error message (i.e. nrerror). These routines were published in W. H. Press, B. P. Flannery, S. A Teukolsky, and W. T. Vetterling, 'Numerical Receipes in C. The Art of Scientific Computing', Cambridge University Press, New York, NY, 1989.
-short_prog_description_end
-short_lib_description
The Cardiac Boundary Imaging (CBI) library function (the C code) performs automated delineation of a left ventricular (LV) boundary in 3D echocardiographic (echo) images. A series of individual echo tomograms is expected in the VIFF (Khoros-specific) format. The system can be executed in two modes: learning and performing. In the learning mode, the images must contain expert LV cavity boundary delineation, and labeled two mitral valve (MV) hinge and one apical (AP) points. In the performing mode, only MV and AP labels are expected. Label means a one pixel dot at a particular location (i.e., exactly 3 labels are expected in each tomogram). A gray scale intensities unique from the rest of the image must be used for outlines and labels, preferably 255 and 254, respectively, in the 8-bit tomograms.
-short_lib_description_end
-man1_long_description
The Cardiac Boundary Imaging (CBI) algorithm uses mapping of LV cavity boundary (i.e. endocardial) surface by means of a mesh of linked points (nodes) in 3D Cartesian coordinates. The CBI is based on gaining a priori knowledge about plausible (average) LV shape and its local variability from expert endocardial outlines of various hearts during a learning proces, and applying this knowledge to selection and delineation of endocardial boundary in 3D (i.e., mapping of endocardial surface) during a performing process. The system learns and stores the knowledge about LV shape by means of vectors. Vectors define an 'average LV model' (a plausible shape of LV surface) with respect to an 'initial hemiellipsoidal model' (flexible hemiellipsoidal surface). The hemiellipsoidal model is formed in first steps of learning by fitting splines into MV and AP points in tomographic scans from different hearts. Iterative execution of the learning algorithm (i.e. presentation of another cardiac expert outlines) increases the number of vectors associated with each node thus providing better mean and SD statistics about LV geometry. Vector values cumulated for each node during iterative learning are stored in a 'reference database' represented by a multidimensional matrix.
The system utilizes knowledge about the plausible LV shape during the performing process by constructing an average model with respect to an

APPENDIX 4-continued initial hemiellipsoidal model created from examined (i.e. previously uknown) data, where the average node positions with their associated 2SD ranges define regions of interest (ROIs) restricts further operations to regions of endocardium. A custom cavity-to-wall transition region (CWTR) detector is employed during the performing process to assess the probability of 'being a boundary point' for each pixel in all tomograms. The CWTR detector is based on order statistics of gray values within a 2D sliding window (kernel). It transforms the original image into an array of probability values (within a range from 0 to 1) where a higher value means the higher probability of a presence of the boundary. The resulting probabilities can be displayed as a CWTR image where cardiac boundaries appear as high-intensity bands. Each node is then translated from its centered position within the corresponding ROI closer to the endocardial boundary using a modified self-organizing map (SOM) algorithm. This, essentially cost-minimizing, method adjusts final position of each node with respect to attraction to spots with highest CWTR values and with respect to neighborhood relationships of nodes. Thus, a final endocardial surface map is generated. Neighborhood spatial relationships and restriction to ROIs are important features that prevent inappropriate placement of nodes or their escape from within the endocardial region.

```
-man1_long_description_end
-man1_examples
-man1_examples_end
-man1_restrictions
Accepts only 1-BYTE (i.e. 8-bit grayscale) images.
-man1_restrictions_end
-man1_see_also
-man1_see_also_end
-man3_long_description
-man3_long_description_end
-man3_restrictions
Accepts only 1-BYTE images.
-man3_restrictions_end
-man3_see_also
som1-9
-man3_see_also_end
-usage_additions
-usage_additions_end
-include_includes
-include_includes_end
-include_additions
-include_additions_end
/* DEFINITION OF IMAGE FORMAT, COLOR MAP, AND INPUT/OUTPUT
STRUCTURES */
-include_macros
#define CHECKINPUT(program, image)
    propertype(program,image,VFF_TYPE_1_BYTE,TRUE);\
    proper_num_images(program,image,1,TRUE);\
    proper_map_enable(program,image,VFF_MAP_OPTIONAL,TRUE);\
-include_macros_end
-main_variable_list
    struct xvimage *image, *end_image, *readimage( );
-main_variable_list_end
-main_before_lib_call
    if (check_args( )) exit(1);
    image = readimage(CBI→i_file); \
    if (image == NULL){ \
       (void) fprintf(stderr, "CBI: cannot read input image\n"); \
       exit(1);\
    }
    CHECKINPUT(program, image);
-main_before_lib_call_end
/* CREATION OF LINKS TO VARIABLES CONTROLED THROUGH THE USER
INTERFACE */
-main_library_call
    if (!ICBI(image, &end_image, CBI→phase_logic,
            CBI→roilrn_logic,
            CBI→delinclr_int,
            CBI→pointclr_int,
            CBI→rep_int,
            CBI→neigh2d_int,
            CBI→neigh3d_int,
            CBI→l_alpha_float,
            CBI→h_alpha_float,
            CBI→algor_toggle,
            CBI→delinitp_logic,
            CBI→nnod_toggle,
            CBI→ws_toggle,
```

APPENDIX 4-continued

```
          CBI→coord_toggle))
    {
      (void) fprintf(stderr, "CBI: library call failed\n");
      sleep (3);
      exit(1);
    }
-main_library_call_end
-main_after_lib_call
(void) writeimage(CBI→o_file, end_image);
-main_after_lib_call_end
-library_includes
-library_includes_end
-library_input
.IP "phase" 15
sets diastolic or systoilic cardiac phase
.IP "roilrn" 15
sets ROI learning or performing mode
.IP "delinclr, pointclr" 15
color (grayscale intensity) of LV delineation and AP/MV points
.IP "rep" 15
number of training repetitions for each node
.IP "neigh2d, neigh3d" 15
neighbors initially considered for SOM formation
.IP "l_alpha, h_alpha" 15
values of a low and high limit of the training parameter alpha
.IP "algor" 15
select classical or modified SOM algorithm
.IP "mode3d" 15
select performance in 2d or 3d mode
.IP "delinitp" 15
resulting outline will be generated using linear or spline interpolation
.IP "nnod" 15
number of nodes in each individual slice
.IP "ws" 15
window size employed in the CWTR detection process
.IP "coord" 15
prints node coordinates in xyz triplets for xprizm3
-library_input_end
-library_output
.IP "prop_image" 15
xvimage structure, the resulting image after cylindrical to
rectangular coordinates conversion.
-library_output_end
/* DECLARATION THE CBI FUNCTION */
-library_def
int
ICBI(image, end_image, phase, roi, delinclr, pointclr, repetitions, neigh2d,
\neigh3d, l_alpha, h_alpha, algorithm, delinitp, nnod, ws, coord)
struct xvimage *image, **end_image;
int phase, roi, delinclr, pointclr, repetitions, neigh2d, neigh3d;
int algorithm, delinitp, nnod, ws, coord;
float l_alpha, h_alpha;
-library_def_end
/* START OF THE C CODE */
-library_code
#define RMAX 2147483647.0
#define pi 3.1415926536
#define LARGE 1.0e30
#define MINI 0.0001
#define CLASSIC 0
#define MODIFIED 1
#define LINEAR 0
#define SPLINE 1
#define PERFORM 0
#define LEARN 1
#define DIASTOLE 0
#define SYSTOLE 1
#define MAXNONODES 49 /* SET THE STANDARD NUMBER OF NODES */
#define MAXNOSLICES 48 */ SET THE STANDARD NUMBER OF SLICES */
{
  FILE *file;
  int register i, j, k, l, m, c, r, s;
  int c1, c2, r1, r2, s1, nd, rg, z, ss;
  int img_cols, img_rows, img_slices, img_slsize, img_volsize;
  int mov_slices, mov_volsize;
  int temp, temp1, temp2, temp_dist, count, flg_count;
  int flg_beg, flg_end;
  int roi_count, roi_count_max;
  int value, value_u, value_d, value_l, value_r;
```

APPENDIX 4-continued

```
    int cycles, num_tr_cycles, cycle_count;
    int n, sum;
    int go, go0, go1, go2, flag;
    int neigh_rad_slc, tmp_neigh_rad_slc, neigh_rad_vol, tmp_neigh_rad_vol;
    int neigh_rad_slc1, neigh_rad_slc2, neigh_rad_vol1, neigh_rad_vol2;
    int ii, tmp_r, tmp_c;
    int numwritten, numread;
    int slch, slcl, nodh, nodl;
    int niter, iterate;
    int elips_radx, elips_rady;
    float yp1=1.0e30;
    float ypn=1.0e30;
    float x, x1, x2, y, y1, y2;
    float x_itsc, y_itsc;
    float mvc, mvr, fs;
    float beta, gama, delta, ang_dif, tmp_ang_dif;
    float radius, radius_hi, radius_lo;
    float *ord_coord, *tmpc_coord, *tmpr_coord;
    float *tmpc_coord2, *tmpr_coord2;
    float *ord1_coord, *regc1_coord, *regr1_coord, *regc1_coord2, *regr1_coord2;
    float *ord2_coord, *regc2_coord, *regr2_coord, *regc2_coord2, *regr2_coord2;
    float *roi_iter;
    float ***roi_x_open, ***roi_y_open, ***roi_x_all, ***roi_y_all;
    float **nod_roi, **gr_cntr;
    float **roi_x_new, **roi_y_new, **roi_x_avg, **roi_y_avg;
    float ***nod_coord, ***nod_coord_init, ***nod_coord_all;
    float ***hilomn_arr;
    float ****roi_loc_vol;
    float fract, tmp_nod, tmp_nod_a, tmp_nod_b, fcycles;
    float sumh, sumv, sumn;
    float aver, stdevx, stdevy;
    float hilomn, hilomn_max;
    float reduc_factor, vect_comp_factor;
    float tmp_alpha, elips_rad, slct;
    float dist, dist1, dist2, short_dist, close_dist, tmp_dist;
    float fmaxnoslices, fmaxnonodes, fslc, fnd, fn, fimg_slices, fnnod;
    float slcl_frc, slch_frc, nodl_frc, nodh_frc;
    float averx, avery, averx2, avery2, sumx, sumy, sumx2, sumy2;
    float x1_is, y1_is, x2_is, y2_is;
    float ic, ir, nc, nr, cc, rr;
    float ftmp_c, ftmp_r, nc_i, nr_i, elips_ratx, elips_raty;
    float m1, m2, min, tmp_min;
    float ang_slc, ang_incr_slc, ang_vol, ang_incr_vol;
    char tmpstr[16];
    char dir[64], filename[64];
    char *program = "ICBI", end;
    char *khome = NULL;
    unsigned char *img_val;
    unsigned char *mov_val; *end_val, *nod_val, *reg_val, *ftr_val, *hit_val;
    struct xvimage *endimage, *nodimage, *regimage, *ftrimage, *hitimage;
    void wire( );
    void hilomean( );
    void conpts1( );
    void conpts2( );
    void place_node( );
    void splin2( );
    void splie2( );
    void spline( );
    void splint( );
    void nrerror( );
    void free_vector( );
    void free_matrix( );
    void free_cube( );
    void free_hypercube( );
    float *vector( ), **matrix( ), ***cube( ), ****hypercube( );
    extern char *getenv( );
    /* SETUP OF A PHASE AND MODE (PROCESS), INTRODUCTORY
CHECKUP */
if(phase==DIASTOLE) printf("\nDIASTOLIC phase,");
if(phase==SYSTOLE) printf("\nSYSTOLIC phase,");
if(roi==PERFORM)   printf("PERFORMING mode.");
if(roi==LEARN)     printf("LEARNING mode.");
printf("\nPlease wait...\n");
if (!(propertype(program, image, VFF_TYP_1_BYTE, FALSE))) {
    (void) fprintf (stderr, "\n\n%s: ", program);
    (void) fprintf (stderr, "Image must be of type 1-BYTE\n");
    sleep(3);
    return (0);
}
```

APPENDIX 4-continued

```
if (!(proper_num_images (program, image, 1, FALSE))) {
  (void) fprintf (stderr, "\n\n%s: ", program);
  (void) fprintf (stderr, "Can only work on files with one image\n\n");
  sleep(3);
  return (0);
}
if (!(h_alpha>l_alpha)) {
  (void) fprintf (stderr, "\n\n%s: ", program);
  (void) fprintf (stderr, "Select h_alpha>l_alpha.\n\n");
  sleep(3);
  return (0);
}
/* IDENTIFICATION OF AN INPUT IMAGE SET */
/*******************************/
/* SEE PROCESS BLOCKS 64 AND 80 */
/*******************************/
img_cols   = image -> row_size;
img_rows   = image -> col_size;
img_slices = image -> num_data_bands;
img_slsize = img_cols*img_rows;
img_volsize = img_slsize*img_slices;
img_val = (unsigned char *)(image->imagedata);
ang_incr_vol = pi/(float)img_slices;
ang_incr_slc = (2*pi)/(float)nnod;
if (!(img_slices>=2)) {
  (void) fprintf (stderr, "\n\n%s: ", program);
  (void) fprintf (stderr, "Volume must contain at least 2 slices.\n\n");
  return (0);
}
  /* IMAGE SPACE ALLOCATION */
     /* ALLOCATE "ENDIMAGE" FOR COMBINED PLACEMENT OF
TRACINGS AND NODES */
    endimage = creatimage(
        (unsigned long) img_rows,
        (unsigned long) img_cols,
        (unsigned long) VFF_TYP_1_BYTE,
        (unsigned long) 1,
        (unsigned long) img_slices,
        "This image contains manual tracings and Kohonen nodes.",
        (unsigned long) 0,
        (unsigned long) 0,
        (unsigned long) VFF_MS_NONE,
        (unsigned long) VFF_MAPTYP_NONE,
        (unsigned long) VFF_LOC_IMPLICIT,
        (unsigned long) 0);
    (if (endimage == NULL)
    {
      fprintf(stderr,
      "\nCBI: Memory for the endimage was not allocated.\n");
      sleep(3);
      return(0);
    }
    end_val = (unsigned char *)(endimage->imagedata);
      /* ALLOCATE "NODIMAGE" FOR PLACEMENT OF NODES WITH
RELATED ROIS */
    \nodimage = createimage(
        (unsigned long) image_rows,
        (unsigned long) img_cols,
        (unsigned long) VFF_TYP_1_BYTE,
        (unsigned long) 1,
        (unsigned long) img_slices,
        "This images contains nodes with related ROIs.",
        (unsigned long) 0,
        (unsigned long) 0,
        (unsigned long) VFF_MS_NONE,
        (unsigned long) VFF_MAPTYP_NONE,
        (unsigned long) VFF_LOC_IMPLICIT,
        (unsigned long) 0);
    if (nodimage == NULL)
    {
      fprintf(stderr,
      "\nCBI: Memory for the nodimage was not allocated.\n");
      sleep(3);
      return(0);
    }
  \nod_val = (unsigned char *)(nodimage->imagedata);
    /* ALLOCATE "REGIMAGE" FOR SHOWING THE INITIAL OUTLINE */
    regimage = creatimage(
        (unsigned long) img_rows,
```

APPENDIX 4-continued

```
      (unsigned long) img_cols,
      (unsigned long) VFF_TYP_1_BYTE,
      (unsigned long) 1,
      (unsigned long) img_slices,
      "This image shows the prohibited region.",
      (unsigned long) 0,
      (unsigned long) 0,
      (unsigned long) VFF_MS_NONE,
      (unsigned long) VFF_MAPTYP_NONE,
      (unsigned long) VFF_LOC_IMPLICIT,
      (unsigned long) 0);
   if (regimage == NULL)
     {
     fprintf(stderr,
     "\nCBI: Memory for the regimage was not allocated.\n");
     sleep(3);
     return(0);
     }
   reg_val = (unsigned char *)(regimage->imagedata);
   /* ALLOCATE ARRAYS */
   n = 5; /* 3 INIT. NODES + 2 DUPLICATES OF THE 1ST AND THE LAST ONE
*/
   roi_iter    = vector(1);
   ord_coord   = vector(n);
   tmpc_coord  = vector(n);
   tmpr_coord  = vector(n);
   tmpc_coord2 = vector(n);
   tmpr_coord2 = vector(n);
   ord1_coord  = vector(n+2);
   regc1_coord = vector(n+2);
   regr1_coord = vector(n+2);
   regc1_coord2 = vector(n+2);
   regr1_coord2 = vector(n+2);
   ord2_coord  = vector(nnod+2);
   regc2_coord = vector(nnod+2);
   regr2_coord = vector(nnod+2);
   regc2_coord2 = vector(nnod+2);
   regr2_coord2 = vector(nnod+2);
     gr_cntr           = matrix(img_slices,2); /* GRAV. CENTER OF AP AND MV
POINTS */
   nod_roi         = matrix(img_slices,nnod); /* ROI RADIUS FOR EACH NODE */
     roi_x_new                = matrix(img_slices,MAXNONODES); /* NEW ROI X
COORDINATES */
     roi_y_new                = matrix(img_slices,MAXNONODES); /* NEW ROI Y
COORDINATES */
     roi_x_avg              = matrix(img_slices,MAXNONODES); /* AVERAGE ROI X
COORD. */
     roi_y_avg              = matrix(img_slices,MAXNONODES); /* AVERAGE ROI Y
COORD. */
   hilomn_arr    = cube(img_slices,img_rows,img_cols); /* HILOMEAN VALUES*/
   nod_coord_init= cube(img_slices,nnod,2); /* INITIAL NODE COORDINATES
*/
     nod_coord_all = cube(img_slices,MAXNONODES,3); /* ALL NODE
COORD,ANG TO GC */
   nod_coord         = cube(img_slices,nnod,5); /* X, Y, SDX, SDY, ROI AREA */
   /* OPEN FILES WITH NUM OF DIASTOLIC AND SYSTOLIC LEARNING
ITERATIONS */
   if((khome=getenv("KHOROS_HOME"))==NULL)
     khome="/usr/khoros";
   sprintf(dir,"%s/marek_toolbox/data",khome);
   if(phase==DIASTOLE) sprintf(filename,"%s/ROI_ITER_D",dir);
   if(phase==SYSTOLE) sprintf(filename,"%s/ROI_ITER_s",dir);
   file=fopen(filename,"r");
   if(file != NULL)
   {
   \numread=fread((char*)roi_iter,sizeof(float),1,file);
   \niter = roi_iter[0];
     printf("\n%d iterations of ROI learning preceded.",
     \niter);
   }
   else if(roi==LEARN)
     {
     printf("\nNO iteration of ROI learning preceded.");
     roi_iter[0]=0.0;
     }
   else
     {
     fprintf(stderr, "\nCould not open the file ROI_ITER.. for reading.\n");
     sleep(3);
```

APPENDIX 4-continued

```
    return(0);
  }
  fclose(file);
  niter = roi_iter[0];
  /* ALLOCATE ARRAYS FOR EXISTING (N) AND FUTURE (N+1) VECTOR
COORDINATES */
  roi_x_open  = cube(niter,MAXNOSLICES,MAXNONODES); /* LOADED ROI
X COORD. */
  roi_y_open  = cube(niter,MAXNOSLICES,MAXNONODES); /* LOADED ROI
Y COORD. */
  roi_x_all   = cube(niter+1,MAXNOSLICES,MAXNONODES); /* ALL ROI X
COORD. */
  roi_y_all   = cube(niter+1,MAXNOSLICES,MAXNONODES); /* ALL ROI Y
COORD. */
  /* OPEN FILES WITH PREVIOUSLY "LEARNED" DIASTOLIC AND
SYSTOLIC VECTORS */
  /***************************/
  /* SEE LOOP 74 and link 76 */
  /***************************/
  if(phase==DIASTOLE) sprintf(filename,"%s/ROI_X_D",dir);
  if(phase==SYSTOLE) sprintf(filename,"%s/ROI_X_S",dir);
  file=fopen(filename,"r");
  if(file != NULL)
    {
      for(j=0; j<niter; j++)
      {
       for(k=0; k<MAXNOSLICES; k++)
       \numread=fread((char*)roi_x_open[j][k],sizeof(float),MAXNONODES,file);
      }
      printf("\n%4d items read from the file ROI_X...",
         j*numread*MAXNOSLICES);
    }
  else if(roi==LEARN)
    {
      printf("\nNO previous ROI_X.. file available.");
    }
  else
    {
      fprintf(stderr,"\nCould not open the file ROI_X.. for reading.\n");
      sleep(3);
      return(0);
    }
  fclose(file);
  if(phase==DIASTOLE) sprintf(filename,"%s/ROI_Y_D",dir);
  if(phase==SYSTOLE) sprintf(filename,"%s/ROI_Y_S",dir);
  file=fopen(filename,"r");
  if(file != NULL)
    {
      for(j=0; j<niter; j++)
      {
        for(k=0; k<MAXNOSLICES; k++)
       \numread=fread((char*)roi_y_open[j][k],sizeof(float),MAXNONODES,file);
      }
      printf("\n%4d items read from the file ROI_Y...\n",
          j*numread*MAXNOSLICES);
    }
  else if(roi==LEARN)
    {
      printf("\nNO previous ROI_Y.. file available.\n");
    }
  else
    {
      fprintf(stderr,"\nCould not open the file ROI_Y.. for reading.\n");
      sleep(3);
      return(0);
    }
  fclose(file);
  /* SET INITIAL VALUES OF VARIABLES, IMAGES AND ARRAYS */
  fimg_slices = img_slices;
  fnnod       = nnod;
  fmaxnoslices = MAXNOSLICES;
  fmaxnonodes = MAXNONODES;
  roi_count_max = 0; /* LARGEST ROI IN ALL SLICES */
  for(i=0; i<image_volsize; i++)
  {
    *(end_val+i) = *(image_val+i);
    *(nod_val+i) = *(img_val+i);
    *(reg_val+i) = 0;
  }
```

APPENDIX 4-continued

```
for(s=0; s<img_slices; s++)
{
 for(r=0; r<img_rows; r++)
 {
  for(c=0; c<img_cols; c++)
  {
   hilomn_arr[s][r][c]=0.0;
  }
 }
}
for(i=0; i<niter; i++)
{
 for(j=0; j<MAXNOSLICES; j++)
 {
  for(k=0; k<MAXNONODES; k++)
  {
   roi_x_all[i][j][k]=roi_x_open[i][j][k];
   roi_y_all[i][j][k]=roi_y_open[i][j][k];
  }
 }
}
/* SLICE-BY-SLICE PROCESSING */
for(s=0; s<img_slices; s++)
{
/* IDENTIFY APICAL (AP) AND MITRAL VALVE (MV) NODES */
/* AND PLACE THEM TO "NOD_COORD" ARRAY. */
  /* THIS IS COMMON FOR BOTH LEARNING AND PERFORMING
PROCESSES */
  /* IMAGE MUST BE ORIENTED WITH THE MV AT THE BOTTOM AND THE
AP AT THE TOP */
 go0 = 1;
 go1 = 2;
 go2 = 3;
 count=0;
 for(r=0; r<img_rows; r++)
 {
  for(c=0; c<img_cols; c++)
  {
  temp = c + r*img_cols + s*img_slsize;
  value = *(img_val+temp);
  if(value==pointclr)
   {
    count++;
   }
   /* GIVE AN ERROR MESSAGE IF MORE THAN 3 LABELS IDENTIFIED */
   if(count>3)
   {
    fprintf(stderr,
    "\nSlice %d: More than 3 expected labels (1xAP, 2xMV) found.\n", s);
    sleep(3);
    return(0);
   }
   /* DETECT APICAL (AP) NODE LOCATION AND ...*/
   if(value==pointclr && go0>0)
   {
    tmpc_coord[2] = nod_coord[s][nnod/2][0] = c;
    tmpr_coord[2] = nod_coord[s][nnod/2][1] = r;
    go0--;
     /* ...REPLACE THE AP POINT BY AN AVERAGE VALUE FROM ITS 4
NEIGHBORS */
        /* I.E. MAKE IT "DISAPPEAR" AFTER FIGURING OUT ITS
COORDINATES */
    sum = *(img_val+temp+1)    + *(img_val+temp-1) +
     *(img_val+temp+img_cols) + *(img_val+temp);
    aver = (float)sum / 4.0;
    *(img_val+temp) = rint(aver);
   }
   /* DETECT LOCATION ONE OF ONE OF THE MITRAL NODES (MV1)
AND... */
   if(value==pointclr && go1>0)
   {
    tmpc_coord[1] = tmpc_coord[4] = nod_coord[s][0][0] = c;
    tmpr_coord[1] = tmpr_coord[4] = nod_coord[s][0][1] = r;
    go1--;
    /* ...MAKE IT DISAPPEAR */
    sum = *(img_val+temp+1)    + *(img_val+temp-1) +
     *(img_val+temp+img_cols) + *(img_val+temp);
    aver = (float)sum / 4.0;
    *(img_val+temp) = rint(aver);
```

APPENDIX 4-continued

```
  }
 /* DETECT LOCATION OF THE OTHER MITRAL NODE (MV2) AND... */
 if(value==pointclr && go2>0)
   {
   tmpc_coord[0] = tmpc_coord[3] = nod_coord[s][nnod-1][0] = c;
   tmpr_coord[0] = tmpr_coord[3] = nod_coord[s][nnod-1][1] = r;
   go2--;
   /* ...MAKE IT DISAPPEAR */
   sum = *(img_val+temp+1)      + *(img_val+temp-1) +
     *(img_val+temp+img_cols) + *(img_val+temp);
   aver = (float)sum / 4.0;
   *(img_val+temp) = rint(aver);
   }
  }
 }
 /* GIVE AN ERROR MESSAGE IF LESS THAN 3 LABELS IDENTIFIED */
  if(count<3)
   {
   fprintf(stderr,
   "\n%Slice %d: Less than 3 labels (AP, MV1, MV2) found.\n", s);
   sleep(3);
   return(0);
   }
 /* GIVE TO THE LEFT (I.E. LOWER X COORD.) MV POINT LOWER ORDER
VALUE */
  if(nod_coord[s][0][0]>nod_coord[s][nnod-1][0])
   {
   tmpc_coord[1] = tmpc_coord[4] = nod_coord[s][nnod-1][0];
   tmpr_coord[1] = tmpr_coord[4] = nod_coord[s][nnod-1][1];
   cc = tmpc_coord[0] = tmpc_coord[3] = nod_coord[s][0][0];
   rr = tmpr_coord[0] = tmpr_coord[3] = nod_coord[s][0][1];
   nod_coord[s][0][0] = nod_coord[s][nnod-1][0];
   nod_coord[s][0][1] = nod_coord[s][nnod-1][1];
   nod_coord[s][nnod-1][0] = cc;
   nod_coord[s][nnod-1][1] = rr;
   }
 /* FIND GRAV. CENTER OF THE AV, MV1, MV2 POINTS, SET THE LV
LONG AXIS */
  gr_cntr[s][0]=rint((tmpc_coord[1]+tmpc_coord[2]+tmpc_coord[3])/3.0);
  gr_cntr[s][1]=rint(((2.0*tmpr_coord[2]+(tmpr_coord[1]+
      tmpr_coord[3])/2.0)/3.0));
 /* LEARNING PROCESS PART 1 */
 /**************************/
 /* SEE LEARNING PROCESS 60 */
 /**************************/
  if(roi==LEARN)
   {
   printf("\nLearning from slice %d (slices 0 - %d).", s, img_slices-1);
 /* FIT SPLINES TO MV AND AP POINTS (INITIAL MODEL) */
 /**********************/
 /* SEE PROCESS BLOCK 66 */
 /**********************/
  for(i=0; i<n; i++) ord_coord[i] = i;
  spline(ord_coord,tmpc_coord,n,yp1,ypn,tmpc_coord2);
  spline(ord_coord,tmpr_coord,n,yp1,ypn,tmpr_coord2);
 /* DETECT AN EXPERT OUTLINE */
  count=0;
  for(i=0; i<img_slsize; i++)
   {
   value = *(img_val+i);
   if(value==delinclr)
     count++;
   }
  if(count==0)
   {
   fprintf(stderr,"\nSlice %d: No delineation detected.\n", s);
   sleep(3);
   return(0);
   }
   /* PROPORTIONALLY DISTRIBUTE THE STANDARD NUMBER OF
NODES */
 /* TO INITIAL POSITIONS */
 /**********************/
 /* SEE PROCESS BLOCK 68 */
 /**********************/
  sumx=sumy=0.0;
  sumx2=sumy2=0.0;
  fract = 2.0/(float)(MAXNONODES-1);
  for(j=0; j<MAXNONODES; j++)
```

APPENDIX 4-continued

```
{
  tmp_nod    = 1.0 + (float)j*fract;
  splint(ord_coord,tmpc_coord,tmpc_coord2,n,tmp_nod,&cc);
  splint(ord_coord,tmpr_coord,tmpr_coord2,n,tmp_nod,&rr);
\nod_coord_all[s][j][0] = cc;
\nod_coord_all[s][j][1] = rr;
/* DEFINE POSITIONAL VECTORS, I.E. FIND NEAREST POINT */
/* ON THE EXPERT OUTLINE FOR EACH NODE */
/***********************/
/* SEE PROCESS BLOCK 70 */
/***********************/
dist = (img_cols>img_rows ? img_cols:img_rows);
for(r=0; r<img_rows; r++)
  {
  for(c=0; c<img_cols; c++)
    {
    value = *(img_val+c+r*img_cols+s*img_slsize);
    if(value==delinclr)
      {
      x = c-cc;
      y = r-rr;
      tmp_dist = sqrt(pow(x,2.0)+pow(y,2.0));
      if(tmp_dist<dist)
        {
        dist=tmp_dist;
        roi_x_new[s][j]=x;
        roi_y_new[s][j]=y;
        }
      }
    }
  }
 }
  sumx = sumx+roi_x_new[s][j];
  sumy = sumy+roi_y_new[s][j];
  sumx2 = sumx2+pow(roi_x_new[s][j],2.0);
  sumy2 = sumy2+pow(roi_y_new[s][j],2.0);
 }
 averx = sumx/MAXNONODES;
 avery = sumy/MAXNONODES;
 averx2= sumx2/MAXNONODES;
 avery2= sumy2/MAXNONODES;
 stdevx= sqrt(fabs(averx2-pow(averx,2.0)));
 stdevy= sqrt(fabs(avery2-pow(avery,2.0)));
 averx=fabs(averx);
 avery=fabs(avery);
 for(j=1; j<MAXNONODES-1; j++)
   {
   x=fabs(roi_x_new[s][j]);
   y=fabs(roi_y_new[s][j]);
   if(x>averx+2.0*stdevx)
     roi_x_avg[s][j]=(roi_x_news[s][j-1]+averx+roi_x_new[s][j+1])/3.0;
   else roi_x_avg[s][j]=roi_x_new[s][j];
   if(y>avery+2.0*stdevy)
     roi_y_avg[s][j]=(roi_y_new[s][j-1]+avery+roi_y_new[s][j+1])/3.0;
   else roi_y_avg[s][j]=roi_y_new[s][j];
   }
   for(j=1; j<MAXNONODES-1; j++)
    {
    roi_x_news[s][j]=roi_x_avg[s][j];
    roi_y_news[s][j]=roi_y_avg[s][j];
    }
 }/* END OF LEARNING PROCESS PART 1 */
/* PERFORMING PROCESS PART 1 */
/***************************/
/* SEE PERFORMING PROCESS 62 */
/***************************/
if(roi==PERFORM)
  {
  printf("\nInitial node position setting in slice %d (slices 0 - %d).",
  s, img_slices-1);
  /* FIT SPLINES TO MV AND AP POINTS (INITIAL MODEL) */
  /***********************/
  /* SEE PROCESS BLOCK 82 */
  /***********************/
  for(i=0; i<n; i++)
    {
    ord_coord[i] = i;
    regc1_coord[i+1] = tmpc_coord[i];
    regr1_coord[i+1] = tmpr_coord[i];
    }
```

APPENDIX 4-continued

```
for(i=0; i<n+2; i++) ord1_coord[i] = i;
spline(ord_coord,tmpc_coord,n,yp1,ypn,tmpc_coord2);
spline(ord_coord,tmpr_coord,n,yp1,ypn,tmpr_coord2);
/* THE FOLLOWING CODE DELINEATES A REGION AMONG THE TWO
*/
/* MV POINTS AND A POINT AT PROXIMAL ⅔ OF THE LV LONG AXIS
BY */
/* FITTING SPLINES. THIS APPROXIMATES AN AREA OF MV MOTION.*/
regc1_coord[6] = regc1_coord[3] = regc1_coord[0] = gr_cntr[s][0];
regr1_coord[6] = regr1_coord[3] = regr1_coord[0] = gr_cntr[s][0];
spline(ord1_coord,regc1_coord,n+2,yp1,ypn,regc1_coord2);
spline(ord1_coord,regr1_coord,n+2,yp1,ypn,regr1_coord2);
ic = regc1_coord[1];
ir = regr1_coord[1];
count=1;
do{  /* THIS ALGORITHM ASSURES CONTINUOUS OUTLINE */
  go = 0;
  flag = 1;
  fract = 3.0/(500.0*(float)count);
  for(i=0; i<(500*count) && flag==1; i++)
   {
   tmp_nod = 1.0 + (float)i*fract;
   splint(ord1_coord,regc1_coord,regc1_coord2,n+2,tmp_nod,&nc);
   splint(ord1_coord,regr1_coord,regr1_coord2,n+2,tmp_nod,&nr);
   dist = sqrt(pow((nc-ic),2.0)+pow((nr-ir),2.0));
   if(dist>1.0)
     {
     go = 1;
     flag = 0;
     ic = regc1_coord[1];
     ir = regr1_coord[1];
     }
    else
     {
     c1 = ic = nc;
     r1 = ir = nr;
     if(c1>0 && c1<img_cols && r1>0 && r1<img_rows)
       {
       temp = c1 + r1*img_cols + s*img_slsize;
       *(reg_val+temp) = 250;
       }
     }
   }
  count++;
  }
 while(go==1);
    /* A MASK OF A REGION PROHIBITED FOR ENDOCARDIAL EDGE
DETECTION IS */
   /* DEFINED BY FILLING THE ABOVE DESCRIBED AREA WITH PIXELS
OF A SAME */
   /* VALUE. THIS AVOIDS CONFUSION OF THE BOUNDARY DETECTION
*/
   /* ALGORITHM BY MV EDGES. */
   for (r=0; r<img_rows; r++)
   {
   flg_beg = 0;
   flg_end = 0;
   for(c=0; c<img_cols; c++)
   {
   temp = c + r*img_cols + s*img_slsize;
   value = *(reg_val+temp);
   if(value==250 && flg_beg==1)
    {
    c2=c;
    flg_end=1;
    }
   if(value==250 && flg_beg==0)
    {
    c1=c;
    flg_beg=1;
    }
   }
   if(flg_beg==1 && flg_end==1)
     conpts2(reg_val, c1, r, c2, r, img_cols, img_rows, s, 250);
   }
    /* DISTRIBUTE THE NODES TO AVERAGE POSITIONS (AVERAGE
MODEL) */
   /*********************/
   /* SEE PROCESS BLOCK 84 */
```

APPENDIX 4-continued

```
/**********************/
fract = 2.0/(float)(nnod-1);
for(i=0; i<nnod; i++)
{
tmp_nod = 1.0 + (float)i*fract;
splint(ord_coord,tmpc_coord,tmpc_coord2,n,tmp_nod,&cc);
splint(ord_coord,tmpr_coord,tmpr_coord2,n,tmp_nod,&rr);
nod_coord[s][i][0] = cc;
nod_coord[s][i][1] = rr;
}
fs   = s;
fslc = fs*((fmaxnoslices-1.0)/(fimg_slices-1.0));
slcl = fslc;
slch = slcl+1;
if(slch==MAXNOSLICES) slch=MAXNOSLICES-1;
slcl_frc = fslc-slcl;
for(i=0; i<nnod; i++)
{
roi_count=0;
fn   = i;
fnd = fn*((fmaxnonodes-1.0)/(fnnod-1.0));
nodl = fnd;
nodh = nodl+1;
if(nodh==MAXNONODES) nodh = MAXNONODES-1;
nodl_frc = fnd-nodl;
sumx=sumy=0.0;
sumx2=sumy2=0.0;
for(j=0; j<niter; j++)
{
x1 = roi_x_all[j][slcl][nodl]+nodl_frc*
  (roi_x_all[j][slcl][nodh]-roi_x_all[j][slcl][nodl]);
x2 = roi_x_all[j][slch][nodl]+nodl_frc*
  (roi_x_all[j][slch][nodh]-roi_x_all[j][slch][nodl]);
y1 = roi_y_all[j][slcl][nodl]+nodl_frc*
  (roi_y_all[j][slcl][nodh]-roi_y_all[j][slcl][nodl]);
y2 = roi_y_all[j][slch][nodl]+nodl_frc*
  (roi_y_all[j][slch][nodh]-roi_y_all[j][slch][nodl]);
x = x1+slcl_frc*(x2-x1);
y = y1+slcl_frc*(y2-y1);
sumx = sumx+x;
sumy = sumy+y;
sumx2 = sumx2+pow(x,2.0);
sumy2 = sumy2+pow(y,2.0);
}
averx = sumx/niter;
avery = sumy/niter;
averx2 = sumx2/niter;
avery2 = sumy2/niter;
stdevx = sqrt(fabs(averx2-pow(averx,2.0)));
stdevy = sqrt(fabs(avery2-pow(avery,2.0)));
/* DEFINE ROIS, FIND THE LARGEST ROI */
nod_coord[s][i][0]    = c1 = nod_coord[s][i][0]+averx;
nod_coord_init[s][i][0] = nod_coord[s][i][0];
nod_coord[s][i][1]    = r1 = nod_coord[s][i][1]+avery;
nod_coord_init[s][i][1] = nod_coord[s][i][1];
nod_coord[s][i][2] = rint(2.0*stdevx);
nod_coord[s][i][3] = rint(2.0*stdevy);
elips_radx = nod_coord[s][i][2];
elips_rady = nod_coord[s][i][3];
for(r=-elips_rady; r<=elips_rady; r++)
{
 for(c=-elips_radx; c<=elips_rads; c++)
  {
  dist1=dist2=0.0;
  if(elips_radx!=0) dist1=pow((float)c,2.0)/pow((float)elips_radx,2.0);
  if(elips_rady!=0) dist2=pow((float)r,2.0)/pow((float)elips_rady,2.0);
  dist=dist1+dist2;
  c2=c+c1;
  r2=r+r1;
  if(dist<=1.0 && c2>=0 && c2<img_cols && r2>=0 && r2<img_rows)
    roi_count++; /* NUMBER OF PIXELS IN THE ACTUAL ROI */
  }
}
nod_coord[s][i][4] = roi_count; /* ROI AREA IN PIXELS */
/* FIND THE LARGEST ROI IN ALL SLICES */
if(roi_count>roi_count_max) roi_count_max=roi_count;
}
}/* END OF PERFORMING PROCESS PART 1 */
}/* END OF SLICE-BY-SLICE PROCESSING */
```

APPENDIX 4-continued

```
/* LEARNING PROCESS PART 2 */
/***************************/
/* SEE LEARNING PROCESS 60 */
/***************************/
if(roi==LEARN)
  {
  /* UPDATE STANDARD DATABASE OF POSITIONAL VECTORS */
  /************************/
  /* SEE PROCESS BLOCK 72 */
  /************************/
  printf("\n");
  for(s=0; s<MAXNOSLICES; s++)
  {
  fs  = s;
  fslc = fs*((fimg_slices-1.0)/(fmaxnoslices-1.0));
  slcl = fslc;
  slch = slcl+1;
  slcl_frc = fslc-slcl;
  if(slch==img_slices) slch = img_slices-1;
  for(i=0; i<MAXNONODES; i++)
  {
    roi_x_all[niter][s][i]=roi_x_new[slcl][i]+slcl_frc*
      (roi_x_new[slch][i]-roi_x_new[slcl][i]);
    roi_y_all[niter][s][i]=roi_y_new[slcl][i]+slcl_frc*
      (roi_y_new[slch][i]-roi_y_new[slcl][i]);
   }
  }
  /* UPDATE THE NUMBER OF LEARNING ITERATIONS */
  roi_iter[0]+=1.0;
  niter=roi_iter[0];
  /* GENERATE OUTPUT DATA FILES OF POSITIONAL VECTORS */
  if(phase==DIASTOLE) sprintf(filename,"%s/ROI_ITER_D",dir);
  if(phase==SYSTOLE) sprintf(filename,"%s/ROI_ITER_S",dir);
  file=fopen(filename,"w+");
  if(file != NULL)
   {
   \numwritten=fwrite((char*)roi_iter,sizeof(float),1,file);
     printf("\n%1d iterations of ROI learning completed.\n", niter);
    }
   else
    {
      fprintf(stderr,"\nCould not open the file ROI_ITER.. for writing.\n");
      sleep(3);
      return(0);
    }
   fclose(file);
   if(phase==DIASTOLE) sprintf(filename,"%s/ROI_X_D",dir);
   if(phase==SYSTOLE) sprintf(filename,"%s/ROI_X_S",dir);
   file=fopen(filename,"w+");
   if(file != NULL)
    {
    for(j=0; j<niter; j++)
      {
        for(k=0; k<MAXNOSLICES; k++)
        \numwritten=fwrite((char*)roi_x_all[j][k],sizeof(float),
            MAXNONODES,file);
      }
      printf("\n%4d items written to the file ROI_X...",
      j*numwritten*MAXNOSLICES);
    }
   else
    {
      fprintf(stderr,"\nCould not open the file ROI_Y.. for writing.\n");
      sleep(3);
      return(0);
    }
   fclose(file);
   if(phase==DIASTOLE) sprintf(filename,"%s/ROI_Y_D",dir);
   if(phase==SYSTOLE) sprintf(filename,"%s/ROI_Y_S",dir);
   file=fopen(filename,"w+");
   if(file != NULL)
          {
              for(j=0; j<niter; j++)
                  {
                      for(k=0; k<MAXNOSLICES; k++)
                      numwritten=fwrite((char*)roi_y_all[j][k], sizeof(float),
                          MAXNONODES,file);
                  }
                  printf("\n%4d items written to the file ROI_Y . . .",
```

APPENDIX 4-continued

```
j*numwritten*MAXNOSLICES);
        }
    else
        {
            fprintf(srderr,"\nCould not open the file ROI_Y . . for writing.\n");
            sleep(3);
            return(0);
        }
    fclose(file);
/* CREATE DATA FOR DISPLAY OF ROIS OF ALL 49 NODES PER
SLICE */
  for(s=0; s<img_slices; s++)
  {
    fs   = s;
    fslc = fs*((fmaxnoslices-1.0)/(fimg_slices-1.0));
    slcl = fslc;
    slch = slcl+1;
    if(slch==MAXNOSLICES) slch=MAXNOSLICES-1;
    slcl_frc = fslc-slcl;
    for(i=0; i<MAXNONODES; i++)
    {
    /* CALCULATE AVERAGE POSITION AND ROI OF EACH NODE (FOR
DISPLAY) */
      sumx=sumy=0.0;
      sumx2=sumy2=0.0;
      for(j=0; j<niter; j++)
      {
        x = roi_x_all[j][slcl][i]+slcl_frc*
          (roi_x_all[j][slch][i]-roi_x_all[j][slcl][i]);
        y = roi_y_all[j][slcl][i]+slcl_frc*
          (roi_y_all[j][slch][i]-roi_y_all[j][slcl][i]);
        sumx = sumx+x;
        sumy = sumy+y;
        sumx2 = sumx2+pow(x,2.0);
        sumy2 = sumy2+pow(y,2.0);
      }
      averx = sumx/niter;
      avery = sumy/niter;
      averx2= sumx2/niter;
      avery2= sumy2/niter;
      stdevx= sqrt(fabs(averx2-pow(averx,2.0)));
      stdevy= sqrt(fabs(avery2-pow(avery,2.0)));
    /* CREATE IMAGE FILE WITH NODES AND THEIR ROIS */
      c1=averx+nod_coord_all[s][i][0];
      r1=avery+nod_coord_all[s][i][1];
      elips_radx=rint(2.0*stdevx);
      elips_rady=rint(2.0*stdevy);
      for(r=-elips_rady; r<=elips_rady; r++)
      {
        for(c=-elips_radx; c<=elips_radx; c++)
        {
         dist1=dist2=0.0;
         if(elips_radx>0) dist1=pow((float)c,2.0)/pow((float)elips_radx,2.0);
         if(elips_rady>0) dist2=pow((float)r,2.0)/pow((float)elips_rady,2.0);
         dist=dist1+dist2;
         c2=c+c1;
         r2=r+r1;
         if(dist<=1.0 && c2>=0 && c2<img_cols && r2>=0 && r2<img_rows)
           {
           value = *(nod_val+c2+r2*img_cols+s*img_slsize);
           *(nod_val+c2+r2*img_cols+s*img_slsize) = 255;
           }
        }
      }
      place_node(nod_val,c1,r1,s,img_cols,img_rows,img_slices);
    }
  }
  *end_image = nodimage;
  }/* END OF LEARNING PROCESS PART 2 */
/* PERFORMANING PROCESS PART 2 */
/***************************/
/* SEE PERFORMING PROCESS 62 */
/***************************/
if(roi==PERFORM)
  {
  printf("\n\nMemory allocation for ROIs and feature processing.");
  printf("\nPlease wait...");
  /* ALLOCATE SPACE FOR ALL ROIS */
  roi_loc_vol = hypercube(img_slices,nnod,roi_count_max,3);
```

APPENDIX 4-continued

```
  for(s=0; s<img_slices; s++)
  {
   for(i=0; i<nnod; i++)
   {
    for(l=0; l<roi_count_max; l++)
    {
    roi_loc_vol[s][i][l][0]=-1.0;
    roi_loc_vol[s][i][l][1]=-1.0;
    roi_loc_vol[s][i][l][2]= 0.0;
    }
   }
  }
  /* DEFINE INDIVIDUAL ROIS, NORMALIZE THEIR SIZE */
  for(s=0; s<img_slices; s++)
  {
   for(i=0; i<nnod; i++)
   {
   /* DEFINE PIXELS ENCOMPASSED IN INDIVIDUAL ROIS */
   c1=nod_coord[s][i][0];
   r1=nod_coord[s][i][1];
   elips_radx=nod_coord[s][i][2];
   elips_rady=nod_coord[s][i][3];
   count=0;
   for(r=-elips_rady; r<=elips_rady; r++)
   {
    for(c=-elips_radx; c<=elips_radx; c++)
    {
    dist1=dist2=0.0;
    if(elips_radx!=0) dist1=pow((float)c,2.0)/pow((float)elips_radx,2.0);
    if(elips_rady!=0) dist2=pow((float)r,2.0)/pow((float)elips_rady,2.0);
    dist=dist1+dist2;
    c2=c+c1;
    r2=r+r1;
    if(dist<=1.0 && c2>=0 && c2<img_cols && r2>=0 && r2<img_rows)
     {
     roi_loc_vol[s][i][count][0]=c2; /* COLUMN COORDINATE */
     roi_loc_vol[s][i][count][1]=r2; /* ROW COORDINATE */
     roi_loc_vol[s][i][count][2]=1.0; /* FLAG (START OF BLANK ARRAY) */
     count++;
     }
    }
   }
   }
  }
  /* CWTR DETECTION PROCESS CONTAINING THE HILOMEAN FILTER
*/
  /***********************/
  /* SEE PROCESS BLOCK 72 */
  /***********************/
   hilomn_max = 0.0;
   for(i=0; i<nnod; i++)
   {
    for(j=0; j<roi_count_max; j++)
    {
    if(roi_loc_vol[s][i][j][2]==1.0)
     {
     c=roi_loc_vol[s][i][j][0];
     r=roi_loc_vol[s][i][j][1];
     if(!(c-ws/2<0||c+ws/2>img_cols-1||r-ws/2<0||r+ws/2>img_rows-1))
      {
      hilomean(img_val, c, r, s, img_cols, img_rows, ws, &hilomn);
      hilomn_arr[s][r][c]=hilomn;
      if(hilomn>hilomn_max) hilomn_max=hilomn;
      }
     }
    }
   }
  }
  /* ALLOCATES SPACE FOR THE FEATURE IMAGE CONTAINING CWTR
VALUES */
  ftrimage = createimage(
    (unsigned long) img_rows,
    (unsigned long) img_cols,
    (unsigned long) VFF_TYP_1_BYTE,
    (unsigned long) 1,
    (unsigned long) img_slices,
    "This is a feature image.",
    (unsigned long) 0,
    (unsigned long) 0,
    (unsigned long) VFF_MS_NONE,
```

APPENDIX 4-continued

```
      (unsigned long) VFF_MAPTYP_NONE,
      (unsigned long) VFF_LOC_IMPLICIT,
      (unsigned long) 0);
  if (ftrimage == NULL)
   {
   fprintf(stderr,
   "\nCBI: Memory for the ftrimage was not allocated.\n");
   sleep(3);
   return(0);
   }
  ftr_val = (unsigned char *)(ftrimage->imagedata);
  /* PROCESS IMAGE WITH THE HILOMEAN FILTER */
  /***********************/
  /* SEE PROCESS BLOCK 44 */
  /***********************/
  for(s=0; s<img_slices; s++)
  {
    for(i=0; i<nnod; i++)
    {
    flag = 1;
    for(j=0; j<roi_count_max; j++)
     {
     if(roi_loc_vol[s][i][j][2]==1.0)
      {
      c=roi_loc_vol[s][i][j][0];
      r=roi_loc_vol[s][i][j][1];
        /* MAKE THE HILOMEAN VALUES INCREASE GEOMETRICALLY
FOR MORE */
        /* INTENSE ATRACTION OF NODES TO SPOTS WITH HIGH
PROBABILITY */
        /* OF A BOUNDARY AND NORMALIZE THE VALUES TO [0, 1]. */
        /***********************/
        /* SEE PROCESS BLOCK 46 */
        /***********************/
      hilomn_arr[s][r][c]=
      pow(hilomn_arr[s][r][c],2.0)/pow(hilomn_max,2.0);
      }
     if(roi_loc_vol[s][i][j][2]==0.0)
      {
      if(flag==1)
       {
       count=j; /* BEGINING OF A BLANK ARRAY SECTION */
       flag=0;
       }
      roi_loc_vol[s][i][j][0]=roi_loc_vol[s][i][j-count][0];
      roi_loc_vol[s][i][j][1]=roi_loc_vol[s][i][j-count][1];
      roi_loc_vol[s][i][j][2]=1.0; /* FILL A BLANK IN THE ARRAY */
      }
     }
    }
  }
  /* MULTIPLY NORMALIZED HILOMEAN VALUES BY 255 */
  /***********************/
  /* SEE PROCESS BLOCK 50 */
  /***********************/
  for(s=0; s<img_slices; s++)
   {
   for(r=0; r<img_rows; r++)
    {
    for(c=0; c<img_cols; c++)
     {
     temp = c + r*img_cols + s*img_slsize;
     value= hilomn_arr[s][r][c]*255.0;
     *(ftr_val+temp) = value;
     }
    }
   }
   /* DEFINE HIT IMAGE WHICH WILL SHOW RANDOMLY SELECTED
PIXELS IN ROIS */
   hitimage = createimage(
       (unsigned long) img_rows,
       (unsigned long) img_cols,
       (unsigned long) VFF_TYP_1_BYTE,
       (unsigned long) 1,
       (unsigned long) img_slices,
       "This is a hit image - shows randomly selected pixels.",
       (unsigned long) 0,
       (unsigned long) 0,
       (unsigned long) VFF_MS_NONE,
```

APPENDIX 4-continued

```
    (unsigned long) VFF_MAPTYP_NONE,
    (unsigned long) VFF_LOC_IMPLICIT,
    (unsigned long) 0);
if (hitimage == NULL)
  {
  fprintf(stderr,
  "\nCBI: Memory for the hitimage was not allocated.\n");
  sleep(3);
  return(0);
  }
hit_val = (unsigned char *)(hitimage→imagedata);
for(i=0; i<img_volsize; i++) *(hit_val+i)=*(reg_val+i);
    /* ADJUST NODE POSITIONS USING THE KOHONEN
SELF-ORGANIZING MAP (SOM) */
/***********************/
/* SEE PROCESS BLOCK 86 */
/***********************/
  neigh_rad_vol = neighd; /* CONSIDERED NEIGHBORS ACROSS SLICES
*/
  neigh_rad_slc = neigh2d; /* CONSIDERED NEIGHBORS WITHIN SLICES
*/
  fcycles=cycles=num_tr_cycles=repetitions*nnod*img_slices; /* # CYCLES
*/
  printf("\n\n%d training cycles follow.",cycles);
  printf("\nPlease wait...");
  cycle_count=0;
  /* SOM TRAINING CYCLES */
  while(num_tr_cycles>0)
  }
    /* REDUCTION FACTOR - APPROACHES ZERO DURING TRAINING
CYCLES */
    if(cycles==1) reduc_factor = 1.0;
    else reduc_factor = ((float)num_tr_cycles-1)/(fcycles-1.0);
    /* DEFINITION OF THE TRAINING PARAMETER ALPHA AND THE
NEIGHBORHOOD */
    tmp_alpha      = l_alpha + (h_alpha-l_alpha)*reduc_factor;
    tmp_neigh_rad_vol= rint((float)neigh_rad_vol);
    tmp_neigh_rad_slc= rint((float)neigh_rad_slc);
    /* RANDOM PIXEL SELECTION FROM WITHIN A ROI */
    ss = rint((double)(rand( )/RMAX)*(float)(img_slices-1));
    \nd = rint((double)(rand( )/RMAX)*(float)(nnod-1));
    rg = rint((double)(rand( )/RMAX)*(float)(roi_count_max-1));
    c1 = ic = roi_loc_vol[ss][nd][rg][0];
    r1 = ir = roi_loc_vol[ss][nd][rg][1];
    temp = c1 + r1*img_cols + ss*img_slsize;
    value = *(reg_val+temp);
    /* AVOID THE PROHIBITED MV REGION USING THE MASK */
    while(!(value==0))
    {
    ss = rint((double)(rand( )/RMAX)*(float)(img_slices-1));
    nd = rint((double)(rand( )/RMAX)*(float)((nnod-1));
    rg = rint((double)(rand( )/RMAX)*(float)(roi_count_max-1));
    c1 = ic = roi_loc_vol[ss][nd][rg][0];
    r1 = ir = roi_loc_vol[ss][nd][rg][1];
    temp = c1 + r1*img_cols + ss*img_slsize;
    value = *(reg_val+temp);
    }
    /* MARK HITS IN THE HIT IMAGE */
    *(hit_val + c1 + r1*img_cols + ss*img_slsize) = 200;
    /* WEIGHT INDIV. PIXELS - THIS WILL DEFINE NODE ATTRACTION
*/
    hilomn = hilomn_arr[ss][r1][c1]; /* HILOMEAN VALUES NORM. TO [0, 1]
*/
    iterate = hilomn*10.0;
    /* PRESENT HIGHLY WEIGHTED PIXELS MORE OFTEN */
    while(iterate>0)
    {
    /* TRAIN THE SOM ACROSS SLICES WHILE ADJUSTING NODE
POSITIONS */
    for(k=-tmp_neigh_rad_vol; k<=tmp_neigh_rad_vol; k++)
    {
    flag = 0;
    s    = ss+k;
    if(s<0)
    {
    flag = 1;
    s    = img_slices+s;
    ic   = img_cols-1-ic;
    }
```

APPENDIX 4-continued

```
    if(s>img_slices-1)
    {
    flag = 1;
        s  = s-img_slices;
    ic  = img_cols-1-ic;
    }
    /* FIND THE WINNING NODE (WINNER) IN THE ACTUAL SLICE */
    /* AS A NEAREST NODE */
    short_dist = LARGE;
    for(i=0; i<nnod; i++)
    {
\nc = nod_coord[s][i][0];
\nr = nod_coord[s][i][1];
    dist = sqrt(pow(ic-nc,2.0)+pow(ir-nr,2.0));
    if(dist<short_dist)
    {
     short_dist = dist;
     ii = i;
    }
    }
    /* TRAIN THE SOM WITHIN THE SLICE WHILE ADJUSTING NODE
POSITIONS */
    for(j=-tmp_neigh_rad_slc; j<=tmp_neigh_rad_slc; j++)
    {
    i = ii+j; /* NODE INDEXING */
    if(i<0)   i = 0;
    if(i>nnod-1) i = nnod-1;
  /* SET COORDINATES OF THE WINNER (ii) OR ITS NEIGHBORS (ii+j)
*/
  \nc = nod_coord[s][i][0];
  \nr = nod_coord[s][i][1];
    /* VECTOR COMPONENT FACTOR - REDUCES ATRACTION TO
REMOTE PIXELS */
    ang_vol = ang_incr_vol*abs(k); /* ELEVATION COMPONENT */
    if(ang_vol>pi/2.0) ang_vol=pi/2.0;
    ang_slc = ang_incr_slc*abs(j); /* AZIMUTAL COMPONENT */
    if(ang_slc>pi/2.0) ang_slc=pi/2.0;
    vect_comp_factor = cos(ang_vol)*cos(ang_slc);
    mvc = (ic-nc)*vect_comp_factor;
    mvr = (ir-nr)*vect_comp_factor;
    /* AVAILABLE SOM ALGORITHMS */
    if(algorithm==CLASSIC)
    {
    ftmp_c = nc+tmp_alpha*mvc;
    ftmp_r = nr+tmp_alpha*mvr;
    }
    if(algorithm==MODIFIED)
    {
    /* DEFINE X AND Y AXES OF THE ACTUAL ROI */
    elips_radx=nod_coord[s][i][2];
    elips_rady=nod_coord[s][i][3];
    /* FIND RATIO OF X AND Y AXES OF THE ACTUAL AND WINNING
ROI */
    elips_ratx=nod_coord[s][i][2]/nod_coord[s][ii][2];
    elips_raty=nod_coord[s][i][3]/nod_coord[s][ii][3];
    if(elips_ratx<1.0) /* SQEEZE X VECTOR COMPONENT */
      mvc = mvc*elips_ratx;
    if(elips_raty<1.0) /* SQEEZE Y VECTOR COMPONENT */
      mvr = mvr*elips_raty;
    ftmp_c = nc+tmp_alpha*mvc;
    ftmp_r = nr+tmp_alpha*mvr;
    nc_i = nod_coord_init[s][i][0];
    nr_i = nod_coord_init[s][i][1];
    /* LET NODES MOVE ONLY WITHIN THEIR ASSOCIATED ROIS */
      if(elips_radx!=0)
      dist1=pow(nc_i-ftmp_c,2.0)/pow((float)elips_radx,2.0);
      else
      dist1=pow(nc_i-ftmp_c,2.0);
      if(elips_rady!=0)
      dist2=pow(nr_i-ftmp_r,2.0)/pow((float)elips_rady,2.0);
      else
      dist2=pow(nr_i-ftmp_r,2.0);
      dist=dist1+dist2;
    /* IF ATTRACTION FROM OUTSIDE OF THE ROI, DO NOT MOVE
AT ALL */
      if(dist>1.0)
      {
      ftmp_c = nc;
      ftmp_r = nr;
```

APPENDIX 4-continued

```
    }
  }
  if(ftmp_c<0.0) ftmp_c=0.0;
  if(ftmp_r<0.0) ftmp_r=0.0;
  if(ftmp_c>(float)(img_cols-1)) ftmp_c = img_cols-1;
  if(ftmp_r>(float)(img_rows-1)) ftmp_r = img_rows-1;
  \nod_coord[s][i][0] = ftmp_c;
  \nod_coord[s][i][1] = ftmp_r;
   }
  }
  iterate--;
 }
 cycle_count++;
 num_tr_cycles--;
 }/* END OF TRAINING CYCLES */
 /* GENERATE IMAGE WITH RANDOM HITS - INTENDED FOR TESTING
PURPOSES */
 /* writeimage("hitimage", hitimage); */
 /* GENERATE A WIRE FRAME DATA SET WITH NODE COORDINATES
*/
 /***********************/
 /* SEE PROCESS BLOCK 88 */
 /***********************/
 if(coord==1 || coord==2)
   {
    do{
       wire(nod_coord, img_cols, img_rows, img_slices, nnod, coord);
       printf("\n\nContinue? (y/n) ");
       scanf("%s",&end);
      }
    while(end!='y');
   }
 /* CONNECT NODES WITH STRAIGHT LINES */
 if(delinitp==LINEAR)
   {
    for(s=0; s<img_slices; s++)
      {
       for(i=0; i<nnod-1; i++)
         {
          c1 = nod_coord[s][i][0];
          r1 = nod_coord[s][i][1];
          c2 = nod_coord[s][i+1][0];
          r2 = nod_coord[s][i+1][1];
          conpts2(end_val, c1, r1, c2, r2, img_cols, img_rows, s, delinclr);
          conpts1(ftr_val, c1, r1, c2, r2, img_cols, img_rows, s);
         }
       c1 = nod_coord[s][0][0];
       r1 = nod_coord[s][0][1];
       c2 = nod_coord[s][nnod-1][0];
       r2 = nod_coord[s][nnod-1][1];
       conpts2(end_val, c1, r1, c2, r2, img_cols, img_rows, s, delinclr);
       conpts1(ftr_val, c1, r1, c2, r2, img_cols, img_rows, s);
      }
   }
 /* CONNECT NODES WITH SPLINES */
 if(delinitp==SPLINE)
   {
    for(i=0; i<nnod+2; i++) ord2_coord[i] = i;
    for(s=0; s<img_slices; s++)
      {
       for(i=0; i<nnod; i++)
         {
          regc2_coord[i+1] = nod_coord[s][i][0];
          regr2_coord[i+1] = nod_coord[s][i][1];
         }
       regc2_coord[0] = regc2_coord[1];
       regr2_coord[0] = regr2_coord[1];
       regc2_coord[nnod+1] = regc2_coord[nnod];
       regr2_coord[nnod+1] = regr2_coord[nnod];
       spline(ord2_coord,regc2_coord,nnod+2,yp1,ypn,regc2_coord2);
       spline(ord2_coord,regr2_coord,nnod+2,yp1,ypn,regr2_coord2);
       /* STARTING NODE COORDINATES */
       ic = nod_coord[s][0][0];
       ir = nod_coord[s][0][1];
       /* DRAW SPLINES BETWEEN ADJACENT NODES */
       count=1;
       do{  /* THIS ALGORITHM ASSURES CONTINUOUS DELINEATION */
          go = 0;
          flag = 1;
```

APPENDIX 4-continued

```
        fract = (float)(nnod-1)/(500.0*(float)count);
        for(i=0; i<(500*count) && flag==1; i++)
        {
        tmp_nod = 1.0 + (float)i*fract;
        splint(ord2_coord,regc2_coord,regc2_coord2,nnod+2,tmp_nod,&nc);
        splint(ord2_coord,regr2_coord,regr2_coord2,nnod+2,tmp_nod,&nr);
        dist = sqrt(pow((nc-ic),2.0)+pow((nr-ir),2.0));
        if(dist>1.0)
          {
          go = 1;
          flag = 0;
          ic = nod_coord[s][0][0];
          ir = nod_coord[s][0][1];
          }
        else
          {
          c1 = ic = nc;
          r1 = ir = nr;
          if(c1>0 && c1<img_cols && r1>0 && r1<img_rows)
            {
            temp = c1 + r1*img_cols + s*img_slsize;
            *(end_val+temp) = delinclr;
            *(ftr_val+temp) = delinclr;
            }
          }
        }
        count++;
        }
      while(go==1);
      c1 = nod_coord[s][0][0];
      r1 = nod_coord[s][0][1];
      c2 = nod_coord[s][nnod-1][0];
      r2 = nod_coord[s][nnod-1][1];
      conpts2(end_val, c1, r1, c2, r2, img_cols, img_rows, s, delinclr);
      conpts2(ftr_val, c1, r1, c2, r2, img_cols, img_rows, s, delinclr);
      }
    }
    *end_image = endimage;
        */ GENERATE CWTR IMAGE - INTENDED ONLY FOR TESTING
PURPOSES */
    /***********************/
    /* SEE PROCESS BLOCK 48 */
    /***********************/
    /* writeimage("ftrimage", ftrimage); */
    }/* END OF PERFORMING PROCESS PART 2 */
  printf("\n\nAll done\n\n");
  sleep(2);
  return(1);
}
/* --------------------------- SUBROUTINES --------------------------- */
/* ----------------- write coordinates for wire model----------------- */
void wire(nod_pol, cols, rows, slices, nodes, flag)
float ***nod_pol;
int cols, rows, slices, nodes, flag;
{
  int s, i, j, rct_cols, rct_rows, rct_slices;
  float xx, zz, theta, rad, sumx, sumy, sumz;
  float ***nod_rct, ***cube( );
  \nod_rct = cube(slices,nodes,3); /* x,y,z coord. in a rect. space */
  /* size of the rectangular space */
  rct_cols   = cols;
  rct_rows   = rows;
  rct_slices = cols;
  printf("\nRectangular space: x=%d, y=%d, z=%d",
         rct_cols, rct_rows, rct_slices);
   for(s=0; s<slices; s++)
    {
    for(i=0; i<nodes; i++)
      {
      rad = nod_pol[s][i][0]-(cols-1)/2.0;
      /* front hemicylinder */
      if(rad>0.0)
        theta = pi*((float)s/slices);
      /* rear hemicylinder */
      else
        theta = pi*((float)s/slices)+pi;
      /* Cartesian coord., here, origin is in the middle (!) */
      xx = fabs(rad)*cos(theta);
      zz = fabs(rad)*sin(theta);
```

APPENDIX 4-continued

```
     \nod_rct[s][i][0]=(rct_cols-1)/2.0+xx;
     \nod_rct[s][i][1]=(rows-1)-nod_pol[s][i][1];
     \nod_rct[s][i][2]=rct_slices-1-((rct_slices-1)/2.0-zz);
      }
    }
/* calculate an average AP node position */
if(flag==1)
 {
  sumx = sumy = sumz = 0.0;
   for(s=0; s<slices; s++)
   {
   sumx += nod_rct[s][nodes/2][0];
   sumy += nod_rct[s][nodes/2][1];
   sumz += nod_rct[s][nodes/2][2];
   }
   for(s=0; s<slices; s++)
   {
   nod_rct[s][nodes/2][0] = sumx/(float)slices;
   nod_rct[s][nodes/2][1] = sumy/(float)slices;
   nod_rct[s][nodes/2][2] = sumz/(float)slices;
   }
 }
/* print x, y, z coordinates along nodes ("vertically") */
printf("\n\nNode coordinates in 3D");
printf("\n\nvertical wires → xprizm3 rows: %d", 2*slices);
  for(s=0; s<slices; s++)
  {
  printf("\n");
  for(i=0; i<=nodes/2; i++)
   {
   printf("\n %6.2f %6.2f %6.2f",
   \nod_rct[s][i][0], nod_rct[s][i][1], nod_rct[s][i][2]);
   }
  }
  for(s=0; s<slices; s++)
  {
  printf("\n");
  for(i=nodes-1; i>=nodes/2; i--)
   {
   printf("\n %6.2f %6.2f %6.2f",
   \nod_rct[s][i][0], nod_rct[s][i][1], nod_rct[s][i][2]);
   }
  }
 s=0;
 printf("\n");
 for(i=0; i<=nodes/2; i++)
  {
  printf("\n %6.2f %6.2f %6.2f",
   \nod_rct[s][i][0], nod_rct[s][i][1], nod_rct[s][i][2]);
  }
/* print x, y, z coordinates along slices ("horizontally") */
printf("\nhorizontal wires → xprizm3 rows: %d", (nodes-1)/2+1);
  for(i=0; i<=nodes/2; i++)
  {
  printf("\n");
  for(s=0; s<slices; s++)
   {
   printf("\n %6.2f %6.2f %6.2f",
   \nod_rct[s][i][0], nod_rct[s][i][1], nod_rct[s][i][2]);
   }
   j=nodes-1-i;
   for(s=0; s<slices; s++)
    {
    printf("\n %6.2f %6.2f %6.2f",
     \nod_rct[s][j][0], nod_rct[s][j][1], nod_rct[s][j][2]);
    }
   s=0;
   printf("\n %6.2f %6.2f %6.2f",
     nod_rct[s][i][0], nod_rct[s][i][1], nod_rct[s][i][2]);
  }
}
/* ---------------- feature processing: hilomean filter ------------------ */
void hilomean(data, x, y, z, cols, rows, window, hilomn_out)
unsigned char *data;
int x, y, z, cols, rows, window;
float *hilomn_out;
{
 int register i, j, c, r;
 int slsize, temp, value, count;
```

APPENDIX 4-continued

```
  float hisum, *hi_arr, ftemp;
  float losum, *lo_arr, diff;
  void free_vector( );
  float *vector( );
  slsize = cols*rows;
  hi_arr= vector(window*window);
  lo_arr= vector(window*window);
  count = 0;
  for(r=0; r<window; r++)
   {
    for(c=0; c<window; c++)
     {
      temp = x+c-window/2 + (y+r-window/2)*cols + z*slsize;
      value = *(data+temp);
      hi_arr[count] = value;
      lo_arr[count] = value;
      count++;
     }
   }
  for(i=0; i<window; i++)
   {
    for(j=i+1; j<window*window; j++)
     {
      if(hi_arr[i]<hi_arr[j])
       {
        ftemp = hi_arr[i];
        hi_arr[i] = hi_arr[j];
        hi_arr[j] = ftemp;
       }
      if(lo_arr[i]>lo_arr[j])
       {
        ftemp = lo_arr[i];
        lo_arr[i] = lo_arr[j];
        lo_arr[j] = ftemp;
       }
     }
   }
  hisum = losum = 0.0;
  for(i=0; i<window; i++)
   {
    hisum += hi_arr[i];
    losum += lo_arr[i];
   }
  diff = (hisum/(float)window) - (losum/(float)window);
  *hilomn_out = diff;
}
/* ----------------- connect two points (vers. 1) ------------------------ */
#define TINY 0.0001
void conpts1(data, x1, y1, x2, y2, cols, rows, z)
unsigned char *data;
int x1, y1, x2, y2, cols, rows, z;
{
  int slsize, temp, img_temp, x_bg, x_ed, y_bg, y_ed, x, y, xx, yy, val;
  int total, count, i;
  float x_df, y_df, a, b, **line_arr;
  float **matrix( );
  void free_matrix( );
  slsize = cols * rows;
  x_df = x1 - x2 + TINY;
  y_df = y1 - y2 + TINY;
  b    = y_df/x_df;
  a    = (float)y1 - b * (float)x1;
  x_bg = (x1 < x2 ? x1 : x2);
  y_bg = (y1 < y2 ? y1 : y2);
  x_ed = (x1 > x2 ? x1 : x2);
  y_ed = (y1 > y2 ? y1 : y2);
  total= (x_ed-x_bg+1) + (y_ed-y_bg+1);
  /* allocate an array for line data coordinates (x~0, y~1) and a flag (~2) */
  line_arr=matrix(total, 3);
  for(i=0; i<total; i++) line_arr[i][2]=1.0;
  /* put actual connection into the array */
  count=0;
  for(x = x_bg; x <= x_ed; x++)
   {
    y = (rint)(a + b * (float)x);
    line_arr[count][0]=x;
    line_arr[count][1]=y;
    count++;
   }
```

APPENDIX 4-continued

```
  for(y = y_bg; y <= y_ed; y++)
  {
    x = (rint)(((float)y - a) / b);
    line_arr[count][0]=x;
    line_arr[count][1]=y;
    for(i=0; i<count-1; i++)
    {
      xx=line_arr[i][0];
      yy=line_arr[i][1];
      if(xx==x && yy==y) line_arr[count][2]=0.0;
    }
    count++;
  }
  for(i=0; i<count; i++)
  {
    if(x>=0 && x<cols && y>=0 && y<rows && line_arr[i][2]==1.0)
    {
      x=line_arr[i][0];
      y=line_arr[i][1];
      img_temp = x + y * cols + z * slsize;
      val=*(data + img_temp);
      if(val<=200) *(data + img_temp)=240;
      else *(data + img_temp)=100;
    }
  }
  free_matrix(line_arr,total);
}
#undef TINY
/* -------------------- connect two points (vers. 2) --------------------- */
#define TINY 0.0001
void conpts2(data, x1, y1, x2, y2, cols, rows, z, value)
unsigned char *data;
int x1, y1, x2, y2, cols, rows, z, value;
{
  int slsize, temp, img_temp, x_bg, x_ed, y_bg, y_ed, x, y;
  float x_df, y_df, x_d, y_d, a, b;
  slsize = cols * rows;
  x_df = x1 - x2;
  y_df = y1 - y2;
  b    = y_df / (x_df + TINY);
  a    = (float)y1 - b * (float)x1;
  x_bg = (x1 < x2 ? x1 : x2);
  y_bg = (y1 < y2 ? y1 : y2);
  x_ed = (x1 > x2 ? x1 : x2);
  y_ed = (y1 > y2 ? y1 : y2);
  x_d = x_ed - x_bg;
  y_d = y_ed - y_bg;
  /* draw the actual connection */
  for(x = x_bg; x <= x_ed; x++)
  {
    y = (rint)(a + b * (float)x);
    if(y >= 0 && y < rows)
    {
      img_temp = x + y * cols + z * slsize;
      *(data + img_temp) = value;
    }
  }
  for(y = y_bg; y <= y_ed; y++)
  {
    x = (rint)(((float)y - a) / b);
    if(x >= 0 && x < cols)
    {
      img_temp = x + y * cols + z * slsize;
      *(data + img_temp) = value;
    }
  }
}
#undef TINY
/* -------------- place node in image (for depiction) --------------------- */
void place_node(data, x, y, z, cols, rows, slices)
unsigned char *data;
int x, y, z, cols, rows, slices;
{
  int slsize = cols*rows, val;
  /* LABEL THE NODE POSITION BY "X" */
  if(x>0 && y>0 && x<cols-1 && y<rows-1)
  {
    *(data+x+y*cols+z*slsize)     = 0;
    *(data+x-1+(y-1)*cols+z*slsize) = 0;
```

APPENDIX 4-continued

```
  *(data+x+1+(y-1)*cols+z*slsize) = 0;
  *(data+x-1+(y+1)*cols+z*slsize) = 0;
  *(data+x+1+(y+1)*cols+z*slsize) = 0;
  *(data+x+(y-1)*cols+z*slsize)   = 255;
  *(data+x+1+y*cols+z*slsize)     = 255;
  *(data+x+(y+1)*col+z*slsize)    = 255;
  *(data+x-1+y*cols+z*slsize)     = 255;
  }
else
  {
  printf("\nThe node at x=%d, y=%d, z=%d is at the edge or out of image\n",
  x, y, z);
  }
}
/* ----- The following subroutines are from 'Numerical Recipes' ------------ */
/* ------------------------------- splin2 ------------------------------ */
/* Calculates bicubic spline interpolation */
void splin2(x1a,x2a,ya,y2a,m,n,x1,x2,y)
float x1a[ ],x2a[ ],**ya,**y2a,x1,x2,*y;
int m,n;
{
  int j;
  float *ytmp,*yytmp,*vector( );
  void spline( ),splint( ),free_vector( );
  ytmp=vector(n);
  yytmp=vector(m); /* <<<<<<<<< */
  for (j=0;j<=m-1;j++)
     splint(x2a,ya[j],y2a[j],n,x2,&yytmp[j]);
  spline(x1a,yytmp,m,1.0e30,1.0e30,ytmp);
  splint(x1a,yytmp,ytmp,m,x1,y);
  free_vector(ytmp);
  free_vector(yytmp);
}
/* ---------------------------- splie2 ----------------------------- */
/* Returns second derivatives for bicubic spline interpolation (splin2) */
void splie2(x1a,x2a,ya,m,n,y2a)
float x1a[ ],x2a[ ],**ya,**y2a;
int m,n;
{
  int j;
  void spline( );
  for (j=0;j<=m-1;j++)
     spline(x2a,ya[j],n,1.0e30,1.0e30,y2a[j]);
}
/* ---------------------------- spline ----------------------------- */
/* Arrays x[ ] and y[ ] contain a tabulated function, and yp1 and ypn are
   given 1st derivatives of the interpolating function at points 1 and n */
/* This function returns an array y2[ ] that contains the second derivatives
   of the interpolating function at the tabulated points xi */
void spline(x,y,n,yp1,ypn,y2)
float x[ ],y[ ],yp1,ypn,y2[ ];
int n;
{
  int i,k;
  float p,qn,sig,un,*u,*vector( );
  void nrerror( );
  void free_vector( );
  u=vector(n-1);
  if (yp1 > 0.99e30)
     y2[0]=u[0]=0.0;
  else {
     y2[0] = -0.5;
     u[0]=(3.0/(x[1]-x[0]))*((y[1]-y[0])/(x[1]-x[0])-yp1);
  }
  for (i=1;i<=n-2;i++) {
     sig=(x[i]-x[i-1])/(x[i+1]-x[i-1]);
     p=sig*y2[i-1]+2.0;
     y2[i]=(sig-1.0)/p;
     u[i]=(y[i+1]-y[i])/(x[i+1]-x[i]) - (y[i]-y[i-1])/(x[i]-x[i-1]);
     u[i]=(6.0*u[i]/(x[i+1]-x[i-1])-sig*u[i-1])/p;
  }
  if (ypn > 0.99e30)
     qn=un=0.0;
  else {
     qn=0.5;
     un=(3.0/(x[n-1]-x[n-2]))*(ypn-(y[n-1]-y[n-2])/(x[n-1]-x[n-2]));
  }
  y2[n-1]=(un-qn*u[n-2])/(qn*y2[n-2]+1.0);
  for (k=n-2;k>=0;k--)
```

APPENDIX 4-continued

```
      y2[k]=y2[k]*y2[k+1]+u[k];
   free_vector(u);
}
/* --------------------------- splint -------------------------------- */
/* Given value of x, arrays x[ ], y[ ], and y2[ ], this routine returns y. */
void splint(xa,ya,y2a,n,x,y)
float xa[ ],ya[ ],y2a[ ],x,*y;
int n;
{
   int klo,khi,k;
   float h,b,a,out;
   void nrerror( );
   klo=0;
   khi=n-1;
   while (khi-klo > 1) {
      k=(khi+klo) >> 1;
      if (xa[k] > x) khi=k;
      else klo=k;
   }
   h=xa[khi]-xa[klo];
   if (h ==0.0) nrerror(¢Bad XA input to routine SPLINT");
   a=(xa[khi]-x)/h;
   b=(x-xa[klo])/h;
   *y=a*ya[klo]'b*ya[khi]+((a*a*a-a)*y2a[klo]+(b*b*b-b)*y2a[khi])*(h*h)/6.0;
}
/* ------------------------- nrerror -------------------------------- */
void nrerror(error_text)
char error_text[ ];
{
   void exit( );
   fprintf(stderr,"\nRun-time error...\n");
   fprintf(stderr,"%s\n",error_text);
   fprintf(stderr,"...now exiting to system...\n");
   exit(1);
}
/* --------------------------- vector ------------------------------- */
float *vector(n)
int n;
{
   float *v;
   v=(float *)malloc((unsigned)n*sizeof(float));
   if (!v) nrerror("allocation failure in vector( )");
   return v;
}
/* --------------------------- matrix ------------------------------*/
float **matrix(nr,nc)
int nr,nc;
{
   int i;
   float **m;
   m=(float **) malloc((unsigned)nr*sizeof(float*));
   if (!m) nrerror("allocation failure 1 in matrix( )");
   for(i=0;i<nr;i++) {
      m[i]=(float *) malloc((unsigned) (nc)*sizeof(float));
      if (!m[i]) nrerror("allocation failure 2 in matrix( )");
   }
   return m;
}
/* --------------------------- cube ------------------------------*/
float ***cube(ns,nr,nc)
int ns,nr,nc;
{
   int i,j;
   float ***c;
   c=(float ***) malloc((unsigned)ns*sizeof(float**));
   if (!c) nrerror("allocation failure 1 in cube( )");
   for(i=0;i<ns; i++)
      {
      c[i]=(float **) malloc((unsigned)nr*sizeof(float));
      if (!c[i]) nrerror("allocation failure 2 in cube( )");
      for(j=0;j<nr;j++)
         {
         c[i][j]=(float *) malloc((unsigned)nc*sizeof(float));
         if (!c[i][j]) nrerror("allocation failure 3 in cube( )");
         }
      }
   return c;
}
/* --------------------------- hypercube ------------------------------*/
```

APPENDIX 4-continued

```
float ****hypercube(nt,ns,nr,nc)
int nt,ns,nr,nc;
{
  int g,i,j;
  float ****h;
  h=(float ****) malloc((unsigned)nt*sizeof(float***));
  if (!h) nrerror("allocation failure 1 in hypercube( )");
  for(g=0;g<nt;g++)
   {
    h[g]=(float ***) malloc((unsigned)ns*sizeof(float));
    if (!h[g]) nrerror("allocation failure 2 in hypercube( )");
    for(i=0;i<ns;i++)
     {
      h[g][i]=(float **) malloc((unsigned)nr*sizeof(float));
      if (!h[g][i]) nrerror("allocation failure 3 in hypercube( )");
      for(j=0;j<nr;j++)
       {
        h[g][i][j]=(float *) malloc((unsigned)nc*sizeof(float));
        if (!h[g][i][j]) nrerror("allocation failure 4 in hypercube( )");
       }
     }
   }
  return h;
}
/* -------------------------- free_vector -------------------------------*/
void free_vector(v)
float *v;
{
  if(v != NULL)
    free((char*)(v));
}
/* -------------------------- free_matrix -------------------------------*/
void free_matrix(m,nr)
float **m;
int nr;
{
  int i;
  for(i=0;i<nr;i++) free((char*)(m[i]));
  free((char*)(m));
}
/* -------------------------- free_cube -------------------------------*/
void free_cube(c,ns,nr)
float ***c;
int ns,nr;
{
  int i,j;
  for(i=0;i<ns;i++)
   {
    for(j=0;j<nr;j++)
     {
      free((char*)(c[i][j]));
     }
    free((char*)(c[i]));
   }
  free((char*)(c));
}
/* ------------------------ free_hypercube -----------------------------*/
void free_hypercube(h,nt,ns,nr)
float ****h;
int nt,ns,nr;
{
  int g,i,j;
  for(g=0;g<nt;g++)
   {
    for(g=0;i<ns;i++)
     {
      for(j=0;j<nr;j++)
       {
        free((char*)(h[g][i][j]));
       }
      free((char*)(h[g][i]));
     }
    free((char*)(h[g]));
   }
  free((char*)(h));
}
```

APPENDIX 4-continued

```
-library_code_end
-library_mods
-library_mods_end
```

I claim:

1. A method for producing a cardiac image using a rotatable ultrasonic transducer, the steps comprising:

producing a signal indicative of cardiac phase;

acquiring a series of tomographic data sets as the ultrasonic transducer is continuously rotated through a range of angular orientations, each acquired tomographic data set depicting a cross-section through the subject heart at an angular orientation indicated by the ultrasonic transducer and at a cardiac phase indicated by said signal;

selecting a particular cardiac phase which the cardiac image is to depict;

producing a 3D image data set by selecting from said series of tomographic data sets tomographic data sets acquired at substantially the selected cardiac phase and at different transducer angular orientations;

producing said cardiac image from said 3D image data set.

2. A method for identifying the location of a cardiac cavity boundary in a 3D image data set, the steps comprising:

establishing a reference database which indicates the likely location of a plurality of nodes on the cardiac cavity boundary with respect to a set of cardiac reference locations;

identifying the cardiac reference locations in the 3D image data set;

establishing an initial cardiac cavity boundary by interpolating between the identified cardiac reference locations in the 3D image data set;

establishing regions of interest in the 3D image data set corresponding to the location of each node in the reference database; and calculating a location in each region of interest which represents the most likely location of the cardiac cavity boundary therein.

* * * * *